US011081234B2

(12) United States Patent
Pappada

(10) Patent No.: US 11,081,234 B2
(45) Date of Patent: Aug. 3, 2021

(54) CLINICAL SUPPORT SYSTEMS AND METHODS

(71) Applicant: ANALYTIC DIABETIC SYSTEMS, INC., Fairborn, OH (US)

(72) Inventor: Scott Pappada, Beavercreek, OH (US)

(73) Assignee: Analytic Diabetic Systems, Inc., Fairborn, OH (US)

( * ) Notice: Subject to any disclaimer, the term of this patent is extended or adjusted under 35 U.S.C. 154(b) by 666 days.

(21) Appl. No.: 14/433,501

(22) PCT Filed: Oct. 3, 2013

(86) PCT No.: PCT/US2013/063178

§ 371 (c)(1),
(2) Date: Apr. 3, 2015

(87) PCT Pub. No.: WO2014/055718

PCT Pub. Date: Apr. 10, 2014

(65) Prior Publication Data

US 2015/0227710 A1 Aug. 13, 2015

Related U.S. Application Data

(60) Provisional application No. 61/709,499, filed on Oct. 4, 2012.

(51) Int. Cl.
*G16H 50/20* (2018.01)
*G16H 50/50* (2018.01)
*G16H 70/20* (2018.01)

(52) U.S. Cl.
CPC ............. *G16H 50/20* (2018.01); *G16H 50/50* (2018.01); *G16H 70/20* (2018.01)

(58) Field of Classification Search
CPC ............................... G06Q 50/22; G06Q 50/24
See application file for complete search history.

(56) References Cited

U.S. PATENT DOCUMENTS 5,103,496 A 4/1992 Andres et al.
5,633,954 A 9/1997 Gupta et al.
(Continued)

FOREIGN PATENT DOCUMENTS

KR 1019980025157 7/1998
WO 2007/149533 12/2007
(Continued)

OTHER PUBLICATIONS

Tervonen, A stochastic multicriteria model for evidence-based decision making in drug benefit-risk analysis, Jan. 26, 2011, Statistics in Medicine, 30 1419-1428 (Year: 2011).*
(Continued)

*Primary Examiner* — Rachelle L Reichert
(74) *Attorney, Agent, or Firm* — John J. Brooks, III

(57) ABSTRACT

Embodiments of clinical support systems and methods are disclosed. In one embodiment, methods for clinical performance measurement are disclosed comprising defining a range of acceptable treatment variable values for a treatment variable of a subject, performing a selected intervention, determining an affected treatment variable value and determining a selection performance measure by comparing the affected treatment variable value to the acceptable treatment variable values. In one embodiment, methods for clinical decision training are disclosed comprising defining a treatment variable of a simulated subject, selecting an intervention on the treatment variable, modeling the selected intervention and presenting a visual representation of the selected intervention. In one embodiment, methods for clinical decision support are disclosed comprising defining a treatment variable of a subject, presenting a decision support variable as clinical decision support, performing a selected intervention and determining an affected treatment variable value.

15 Claims, 16 Drawing Sheets

(56) References Cited

U.S. PATENT DOCUMENTS

| | | | | |
|---|---|---|---|---|
| 5,727,128 | A | 3/1998 | Morrison | |
| 6,012,034 | A * | 1/2000 | Hamparian | A61M 5/172 604/95.01 |
| 6,272,480 | B1 | 8/2001 | Tresp et al. | |
| 6,379,301 | B1 | 4/2002 | Worthington et al. | |
| 6,544,212 | B2 | 4/2003 | Galley et al. | |
| 6,572,545 | B2 | 6/2003 | Knobbe et al. | |
| 6,582,366 | B1 | 6/2003 | Porumbescu | |
| 6,601,053 | B1 | 7/2003 | Schaffer et al. | |
| 6,658,396 | B1 | 12/2003 | Tang et al. | |
| 6,882,940 | B2 | 4/2005 | Potts et al. | |
| 6,923,763 | B1 | 8/2005 | Kovatchev et al. | |
| 6,931,327 | B2 | 8/2005 | Goode, Jr. et al. | |
| 7,025,425 | B2 | 4/2006 | Kovatchev et al. | |
| 7,052,472 | B1 | 5/2006 | Miller et al. | |
| 7,230,529 | B2 | 6/2007 | Ketcherside, Jr. et al. | |
| 7,296,005 | B2 | 11/2007 | Minamino et al. | |
| 8,655,822 | B2 * | 2/2014 | Levchuk | G06Q 50/20 706/12 |
| 8,762,306 | B2 | 6/2014 | Cameron et al. | |
| 2003/0060690 | A1 * | 3/2003 | Jelliffe | A61B 5/0205 600/300 |
| 2003/0153821 | A1 | 8/2003 | Berner et al. | |
| 2003/0175806 | A1 | 9/2003 | Rule et al. | |
| 2004/0167418 | A1 | 8/2004 | Nguyen et al. | |
| 2005/0119540 | A1 | 5/2005 | Potts et al. | |
| 2005/0119534 | A1 | 6/2005 | Trost et al. | |
| 2005/0171503 | A1 | 8/2005 | Berghe et al. | |
| 2005/0197554 | A1 | 9/2005 | Polcha | |
| 2005/0234311 | A1 * | 10/2005 | Kouchi | G06F 19/3437 600/300 |
| 2005/0245878 | A1 | 11/2005 | Mernoe et al. | |
| 2006/0264718 | A1 | 11/2006 | Ruchti et al. | |
| 2007/0032706 | A1 | 2/2007 | Kamath et al. | |
| 2007/0078680 | A1 * | 4/2007 | Wennberg | G16H 40/20 705/2 |
| 2007/0208246 | A1 | 9/2007 | Brauker et al. | |
| 2008/0027292 | A1 | 1/2008 | Rosman et al. | |
| 2008/0033254 | A1 | 2/2008 | Kamath et al. | |
| 2008/0082323 | A1 | 4/2008 | Bai et al. | |
| 2008/0189051 | A1 | 8/2008 | Goode et al. | |
| 2008/0221923 | A1 | 9/2008 | Shogan | |
| 2008/0306353 | A1 * | 12/2008 | Douglas | G06F 19/3406 600/301 |
| 2009/0105573 | A1 | 4/2009 | Malecha | |
| 2009/0150183 | A1 | 6/2009 | Schmitt et al. | |
| 2009/0156924 | A1 | 6/2009 | Shariati et al. | |
| 2009/0177143 | A1 | 7/2009 | Markle et al. | |
| 2009/0192366 | A1 | 7/2009 | Mensinger et al. | |
| 2009/0192722 | A1 | 7/2009 | Shariati et al. | |
| 2010/0114237 | A1 * | 5/2010 | Giftakis | A61B 5/0476 607/45 |
| 2010/0280348 | A1 | 11/2010 | Wenzel et al. | |
| 2010/0291604 | A1 | 11/2010 | Rosman et al. | |
| 2010/0292634 | A1 | 11/2010 | Kircher, Jr. et al. | |
| 2011/0016067 | A1 | 1/2011 | Levchuk et al. | |
| 2011/0178820 | A1 * | 7/2011 | Soni | A61B 5/0002 705/3 |
| 2011/0225112 | A1 * | 9/2011 | Cameron | G06F 19/00 706/20 |
| 2012/0277833 | A1 * | 11/2012 | Gerber | A61N 1/36139 607/62 |
| 2013/0317834 | A1 | 11/2013 | Ryan et al. | |
| 2014/0304204 | A1 | 10/2014 | Cameron et al. | |
| 2015/0193583 | A1 | 7/2015 | McNair et al. | |

FOREIGN PATENT DOCUMENTS

| | | | | |
|---|---|---|---|---|
| WO | WO2008131224 | | 10/2008 | |
| WO | WO2010019919 | | 2/2010 | |
| WO | WO-2011060398 | A1 * | 5/2011 | G16H 40/20 |
| WO | 2013126144 | | 8/2013 | |
| WO | 2014/055718 | | 10/2014 | |
| WO | 2017027432 | | 2/2017 | |

OTHER PUBLICATIONS

Oh, Eung Gie, Written Opinion of the International Searching Authority, parent PCT App. No. PCT/US13/063178, dated Jan. 28, 2014, 15 pages, KR.

Becamel, Philippe, International Preliminary Report on Patentability, parent PCT App. No. PCT/US13/063178, dated Apr. 7, 2014, 11 pages, Switzerland.

PCT International Search Report and the Written Opinion, PCT/US2009/53943 filed Aug. 14, 2009, dated Dec. 24, 2009, 6 pgs.

PCT International Preliminary Report on Patentability, PCT/US2009/53943 filed Aug. 14, 2009, dated Feb. 24, 2011, 14 pgs.

Ivanov et. al. 'Temporal Processing Neural Networks for Speech Recognition' In: International Conference on Neural Networks and Artificial Intelligence. Fig. 2 and p. 4, col. 1, para (4), p. 5, col. 1, para (2), p. 7, col. 1, para (7), and p. 8, col. 1, para (4), 9 pgs.

Magoulas et. al. 'Effective Backpropagation Training with Variable Stepsize'. Neural Networks, vol. 10, No. 1, pp. 69-82, 1997, 14 pgs.

Skevolifakas et. al. A Communication and Information Technology Infrastructure for Real Time Monitoring and Management of Type 1 Diabetes Patients. In: Engineering in Medicine and Biology Society, 2007. Aug. 22-26, 2007 pp. 3685-3688.

Oh, Eung Gie, Korean Intellectual Property Office, International Search Report and Written Opinion, PCT App. No. PCT/US2013/063178, dated Jan. 2014, 15 pgs., KR.

Pappada, Scott et. al. "Neural Network Prediction of Glucose in Diabetic Patients Using Continuous Glucose Monitoring (CGM) and an Electronic Intensive Life Event Diary (EILED)", 2006, Department of Bioengineering, University of Toledo, Toledo, Ohio and Northeastern Ohio Universities College of Medicine, Rootstown, Ohio, one (1) page poster, USA.

Chubb, Mikayla, Notice of Allowance and Fees Due, U.S. Appl. No. 13/058,673, dated Jan. 31, 2014, 6 pgs., USPTO, Arlington VA, USA.

Chubb, Mikayla, Non-Final Rejection for U.S. Appl. No. 13/058,673, dated Jul. 25, 2013, 15 pgs., USPTO, Arlington VA, USA.

Pappada, Scott et al, Response to Non-Final Rejection with Affidavit for U.S. Appl. No. 13/058,673, filed Nov. 25, 2013, 73 pgs, USPTO, Arlington VA, USA.

Mikayla Chubb, Notice of Allowance and Fees Due, U.S. Appl. No. 14/284,975, filed May 22, 2014, dated Mar. 10, 2015, pp. 10, USPTO, US.

Mikayla Chubb, Office Action Summary, U.S. Appl. No. 14/284,975, filed May 22, 2014, dated Nov. 5, 2014, pp. 1-11, USPTO.

Wong, Lee W., Written Opinion of the International Searching Authority, PCT App. No. PCT/US16/45938, dated Oct. 24, 2016, 14 pages, US.

Klaus Prank et. al. Predictive neural networks for learning the time course of blood glucose levels. Neural Comp, 1998; 10(4):941-953. Entire document, especially Figs. 1-2 and p. 943, para (2), p. 944, para (4), p. 945, para (1), p. 950, para (3), 13 pgs., Cambridge MA, US.

Volker Tresp et al., Neural Network Models for the Blood Glucose Metabolism of a Diabetic, IEEE Transaction on Neural Networks, Sep. 1999, 24 pgs., vol. 10 Issue 5, Piscataway NJ, US.

Ferrer, Richard et. al. "Empiric Antibiotic Treatment Reduces Mortality in Severe Sepsis and Septic Shock From the First Hour: Results From a Guideline-Based Performance Improvement Program*", Crit Care Med. Aug. 2014;42(8):1749-55, USA, 7 pgs.

Henry, Katharine et. al. "A targeted real-time early warning score (TREWScore) for septic shock", Science Translational Medicine Aug. 5, 2015: vol. 7, Issue 299, pp. 299ra122, 10 pgs.

Donegan, Lee-Ann, "Penn Medicine's "Sepsis Sniffer" Generates Faster Sepsis Care and Suggests Reduced Mortality", Perelman School of Medicine, Pennsylvania, USA, 2 pgs.

Klein, K J., & Kozlowski, S. W. (2000). A multilevel approach to theory and research in organizations: Contextual, temporal, and emergent processes. In K. J. Klein & S. W. J. Kozlowski (Eds.), Multilevel theory, research, and methods in organizations: Foundations, extensions, and new directions (pp. 3-90). San Francisco, CA: Jossey-Bass. 45 pgs.

(56) References Cited

OTHER PUBLICATIONS

Evans, J. S. B. T., & Stanovich, K. (2013). Dual-process theories of higher cognition: Advancing the debate. Perspectives in Psychological Science, 8(3), 223-241. 19 pgs.
Olguin, D. O., Waber, B. N., Kim, T., Mohan, A., Ara, K., & Pentland, A. (2009). Sensible organizations: Technology and methodology for automatically measuring organizational behavior. IEEE Transactions on Systems, Man, and Cybernetics, Part B (Cybernetics), 39(1), 43-55. 13 pgs.
Kamzanova, A. T., Kustubayeva, A. M., & Matthews, G. (2014). Use of EEG workload indices for diagnostic monitoring of vigilance decrement. Human factors, 56(6), 1136-1149. 14 pgs.
Berka, C., Levendowski, D. J., Lumicao, M. N., Yau, A., Davis, G., Zivkovic, V. T., & Craven, P. L. (2007). EEG correlates of task engagement and mental workload in vigilance, learning, and memory tasks. Aviation, space, and environmental medicine, 78(5), B231-B244. 14 pgs.
Kohlmorgen, J., Dornhege, G., Braun, M., Blankertz, B., Müller, K. R., Curio, G., & Kincses, W. (2007). Improving human performance in a real operating environment through real-time mental workload detection. Toward Brain-Computer Interfacing, 409-422. 14 pgs.
Moreno, R. (2010). Cognitive load theory: More food for thought. Instructional Science, 38(2), 135-141. 7 pgs.
Gaba, D. M., & Raemer, D. (2007). The tide is turning: organizational structures to embed simulation in the fabric of healthcare. Simul Healthcare 2007;2: 1-3. 3 pgs.
Niehaus, J., & Riedl, M. O. (2009). Scenario adaptation: An approach to customizing computer-based training games and simulations. In Proceedings of the AIED 2009 Workshop on Intelligent Educational Games (vol. 3, pp. 39-98). 10 pgs.
Paas, F., Renkl, A., & Sweller, J. (2003). Cognitive load theory and instructional design: Recent developments. Educational psychologist, 38(1), 1-4. 4 pgs.
Vygotsky, L. (1978). Interaction between learning and development. Readings on the development of children, 23(3), 34-41. 7 pgs.
Ivanova, A., & Dyankova, E. (2009) Designing a Decision Engine for Adaptive Training Simulators. Proceedings of e-Learning, 9, 207-213. 7 pgs.
Olguin, D. O., Gloor, P. A., & Pentland, A. S. (2009). Capturing individual and group behavior with wearable sensors. In Proceedings of the 2009 aaai spring symposium on human behavior modeling, SSS (vol. 9). 7 pgs.
Olguín-Olguín, D., & Pentland, A. (2010). Sensor-based organisational design and engineering. International Journal of Organisational Design and Engineering, 1(1-2), 69-97. 29 pgs.
Salas, Eduardo, Rosen, Michael A. , Held , Janet D., Weissmuller, Johnny J. (2009) Performance Measurement in Simulation-Based Training: A Review and Best Practices. Simulation Gaming 2009. 49 pgs.
Gevins, A., & Smith, M. E. (2003). Neurophysiological measures of cognitive workload during human-computer interaction. Theoretical Issues in Ergonomics Science, 4(1-2), 113-131. 20 pgs.
Lei, S., & Roetting, M. (2011). Influence of task combination on EEG spectrum modulation for driver workload estimation. Human factors, 53(2), 168-179. 12 pgs.
Funke, G. J., Knott, B. A., Salas, E., Pavlas, D., & Strang, A. J. (2012). Conceptualization and measurement of team workload: A critical need. Human Factors, 54(1), 36-51. 16 pgs.
Oser, R. L., Cannon-Bowers, J. A., Salas, E., & Dwyer, D. J. (1999). Enhancing human performance in technology-rich environments: Guidelines for scenario-based training. Human Technology Interaction in Complex Systems, 9, 175-202. 28 pgs.
Pappada SM, Feeney JJ, Moffat-Bruce SM., Winfield S, Papadimos TJ, A novel measurement technology to improve critical care provider performance and skill acquisition, Society of Critical Care Medicine 46th Critical Care Congress Honolulu, HI, Jan. 2017. 9 pgs.
Pappada SM, Papadimos TJ, Lipps J, Feeney JJ, Durkee KT, Galster SM, Winfield S, Pfeil S, Castellon-Larios K, Bhandary SB, Stoicea N, Moffat-Bruce SM. Establishing an instrumented environment for simulation-based training of healthcare providers: an initial proof of concept. International Journal of Academic Medicine, Jul. 2016. 124 pgs.

* cited by examiner

CLINICAL SUPPORT SYSTEMS AND METHODS

CROSS-REFERENCE TO RELATED APPLICATIONS

This application claims benefit of U.S. Pat. App. No. 61/709,499 filed on Oct. 4, 2012, which is herein incorporated by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

This invention relates to systems and methods to support clinical decision makers, in particular to monitor and model healthcare decisions in various outpatient and inpatient clinical settings or training environments.

2. Description of the Prior Art

Optimal clinical/therapeutic decision making is extremely difficult as a number of factors affect physiological/therapeutic set points of interest.

Current visualization of electronic medical records (EMR) is suboptimal. Health-related information may be present however, presentation, and usability of the EMR data for decision support by even the most experienced clinical staff is extremely difficult.

Multiple clinical decision support systems exist with various algorithms/approaches tailored to provide decision support and feedback. However, clinical decisions support systems known to date lack the comprehensive structure of the disclosed clinical support systems and methods which may provide a more complete picture for decision support. Some embodiments of the disclosed systems and methods provide real-time feedback patients and medical staff such that they can train themselves, learn complex interactions between physiological, treatment, and EMR data and ultimately make optimal decisions leading to the best possible patient outcomes.

One related solution to one initial tested embodiment of The Simulation, Training, And Clinical Decision Support (STACDS) system for optimizing inpatient glycemic control is a solution EndoTool which is developed by Monarch Medical Technologies (monarchmedtech.com/glucose-management-system-com-).

No system is known which combines simulation, training, and clinical decision support with real-time healthcare provider performance feedback in a dual purpose real-time and retrospective tool/environment.

The real-time and historical performance measurement, assessment, and analysis is not available in any applications to date. This can support healthcare staff utilization/allocation, objective performance reviews, education/training, and other key applications.

BRIEF SUMMARY OF THE INVENTION

The following summary is included only to introduce some concepts discussed in the Detailed Description below.

This summary is not comprehensive and is not intended to delineate the scope of protectable subject matter, which is set forth by the claims presented at the end.

In one example embodiment, a computer implemented method for clinical decision modeling is disclosed, the method comprising monitoring at least one treatment variable value, simulating the effect of an intervention on the at least one treatment variable value set point and presenting a representation of the effect of the intervention on the at least one treatment variable value. In some embodiments, the treatment variable value is a therapeutic/physiological set point of the patient.

In one example embodiment, a computer implemented method for clinical performance measurement is disclosed comprising defining a range of an acceptable treatment variable values for a treatment variable of a subject, performing a selected intervention, determining an affected treatment variable value after performing the selected intervention and automatically determining a selection performance measure as the clinical performance measurement of the selected intervention by comparing the affected treatment variable value to the acceptable treatment variable values. Some embodiments further comprise defining a recommended intervention and automatically determining the selection performance measure as the clinical performance measurement of the selected intervention by comparing the affected treatment variable value to the acceptable treatment variable values and comparing the recommended intervention to the selected intervention. Some embodiments further comprise determining a plurality of selection performance measures over a performance time period, each of the selection performance measures associated with one or more time in the performance time period, determining whether one or more of the plurality of selection performance measures is one of a good selection performance measure or a bad selection performance measure and identifying the one or more time wherein the selection performance measure is one of a good selection performance measure or a bad selection performance measure. Some embodiments further comprise automatically determining a recommended intervention as the selected intervention before performing the selected intervention. In some embodiments, automatically determining a recommended intervention comprises automatically determining a recommend intervention utilizing a control system model to model the affected treatment variable value. Some embodiments further comprise identifying performance or treatment indicators by performing a pattern recognition analysis on selected performance measures or on affected treatment variable values.

In one example embodiment, a computer implemented method for clinical decision training is disclosed comprising defining a treatment variable of a simulated subject, selecting an intervention on the treatment variable, modeling the selected intervention on the treatment variable to determine an affected treatment variable value and presenting a visual representation of the affected treatment variable value. In some embodiments, modeling the selected intervention on the treatment variable comprises modeling the selected intervention on the treatment variable with a machine learning algorithm. Some embodiments further comprise, before selecting the intervention on the treatment variable, selecting a test intervention on the treatment variable, inputting the test intervention into a predictive model, determining the affected treatment variable value over a selected time by modeling the test intervention on the affected treatment variable over the selected time and presenting a visual representation of the affected treatment variable value over the selected time. Some embodiments further comprise automatically determining a recommended intervention utilizing a control system model to model the affected treatment variable value.

In one example embodiment, a computer implemented method for clinical decision support is disclosed comprising defining a treatment variable of a subject, presenting at least one decision support variable, performing a selected intervention and determining an affected treatment variable value. Some embodiments further comprise receiving a set of historical treatment variables of the subject, identifying a trend from the historical treatment variables of the subject and the decision support variable comprises the trend. In some embodiments, identifying a trend from the historical treatment variables of the subject further comprises utilizing at least one of a supervised machine learning algorithm and model and an unsupervised machine learning algorithm and model. Some embodiments further comprise further comprise receiving a set of historical treatment variables of the subject, identifying one or more event from the historical treatment variables of the subject, receiving a set of real-time treatment variables of the subject and comparing the one or more event to the set of real-time treatment variables to estimate future expected trends/patterns in treatment variables. Some embodiments further comprise determining a similarity rating between the set of historical treatment variables of the subject and the real-time treatment variables of the subject, defining a similarity rating threshold, identifying one or more of the events that exceed the similarity rating threshold as an exceptional event and statistically analyzing the exceptional event to provide an estimation of a future trend. In some embodiments, presenting a decision support variable comprises presenting at least one of a plurality of interventions on the treatment variable, selecting one of the interventions as a test intervention, inputting the test intervention into a predictive model, determining an affected test treatment variable value over a selected time by modeling the test intervention on the test treatment variable over the selected time and presenting a visual representation of the affected test treatment variable value over the selected time. Some embodiments further comprise determining a selection performance measure.

In one example embodiment, a computer implemented system for clinical support is disclosed, the system comprising a multimodal measurement and assessment layer configured to monitor at least one treatment variable value, a real-time prediction layer configured to simulate the effect of an intervention on the at least one treatment variable value and a user interface configured to present a representation of the effect of the therapeutic intervention on the at least one treatment variable value.

In one embodiment, the computer implemented system for clinical support comprises a STACDS system designed to simulate the effect of interventions and clinical decisions, prediction and pattern recognition of key treatment variable value and adverse outcomes, provide real-time and historical performance feedback for patients and medical staff to ensure that clinical and therapeutic decisions they make lead to optimal outcome and healthcare delivery. This STACDS embodiment may integrate these capabilities into a single system and tool supporting augmented visualization of EMR data and optimization of healthcare delivery via simulation, training, and clinical decision support in both real-time and retrospective settings.

In some embodiments, the treatment variable is an analyte level and the acceptable treatment variable value is a range of the analyte levels.

In some embodiments, the clinical support systems and methods may be implemented and deployed on computers, PCs, laptops, smartphones, tablets, and other useful computing platforms and mobile devices.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1A:
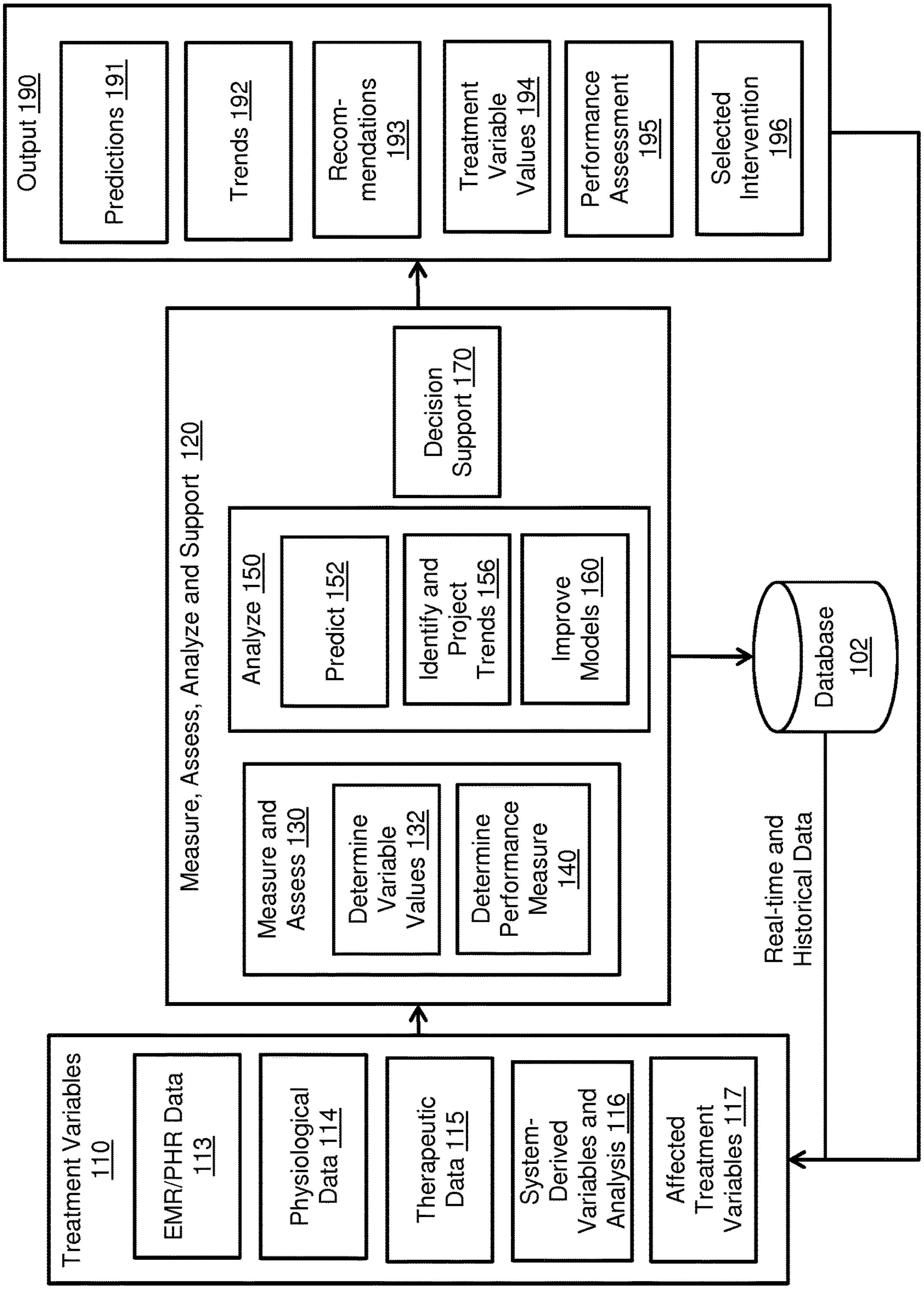
FIG. 1A illustrates a process diagram of one example embodiment of methods for clinical decision support.

Systems and methods for clinical decision support will now be described in detail with reference to the accompanying drawings. It will be appreciated that, while some of the following description focuses on systems and methods that provide clinical decision support regarding glucose levels of a patient, the systems and methods disclosed herein have wide applicability. Notwithstanding the specific example embodiments set forth below, all such variations and modifications that would be envisioned by one of ordinary skill in the art are intended to fall within the scope of this disclosure.

As used herein, set point means a desired or target treatment variable value of a treatment variable.

As used herein, predictions are estimated projections of data values from a certain point in time.

As used herein, an analyte can comprise one or more of: naturally occurring, artificial, metabolites, and/or reaction products. In certain embodiments, the analyte can comprises one or more of: glucose; blood and/or urine components; proteins; amino acids; hormones; cholesterol; viruses; toxins; antibodies; antigens; vitamins; imaging contrast agents; illegal drugs; pharmaceutical compositions; and steroids.

As used herein, an intervention is an action taken to affect a treatment variable of a subject. For example, and not for limitation, interventions may comprise; medication changes (e.g. increasing medication dosage X and decreasing medication dosage Y); subject lifestyle changes in outpatient setting (e.g. changing nutritional intake, exercising, going to bed at a different time); starting a new medication (e.g., will this impact the current treatment variable value or therapeutic set-point the subject is currently monitoring and trying to control); entering a "next" expected value for a particular data point (derived from predictions) to determine efficacy of therapy; or altering the values of any data input in an attempt to alter the values of future data inputs. An intervention may be an actual intervention on a subject or it may be a hypothetical intervention on a subject or in a simulated environment.

Some embodiments of the systems and methods for clinical monitoring and modeling disclose provide a comprehensive simulation, training, and clinical decision support tool which may be utilized in both real-time and retrospectively to enhance/optimize multiple aspects of healthcare delivery and outcome from patient-centered and medical staff-centered perspectives.

In some embodiments, utilizing the disclosed systems' and methods' simulation capabilities, patients/clinician can titrate medications or other interventions to determine the best possible clinical decision leading to the best possible clinical outcomes and feel confident in their decision.

Embodiments of the clinical support systems for outpatient/ambulatory setting are directed to situations where the subject may not be committed to a hospital and the subject is able to live their everyday lives outside of the hospital environment. These settings require an alternate form of data collection and data in this area can be consistent with the type of data in electronic medical records (EMR) but more along of the lines of personal health records, or personal health-related data. There will be less availability for the data to be collected in real-time in an automated fashion as in the hospital setting, thus, data will need to be manually entered into the system. Here example representations of the data that is collected will include but is not limited to lifestyle data, emotional state data, data related to the self-management of the subject's condition and other data documented as part of self-management of their condition. Lifestyle data may include such data as sleep-wake cycles, sleep quality, exercise routines, day to day activities such as housework, working at your job, etc. Emotional state data may include data representing such emotional states as stress, depression, anxiety, etc. Data related to the self-management of a patient's specific condition may include medications and dosages, nutritional intake and monitoring results of the treatment variable in question (e.g. blood glucose for patients with diabetes).

One Example Embodiment of the Clinical Support Methods

Example embodiments of clinical support methods is illustrated in FIG. 1A. As shown, the methods generally comprise methods to accept treatment variables 110, measure, assess, analyze and support those inputs at 120 to provide meaningful output information at 190 to patients and clinicians. The methods to measure, assess, analyze and support 120 may include measurement and assessment methods at 130, analyze methods at 150 and decision support methods at 170. As shown, the treatment variables 110 may comprise any type of treatment variable and the output 190 comprises several different results from the methods. In some embodiments, the methods store data from these methods in a database 102.

One example embodiment of the clinical support methods comprise methods executed by The Simulation, Training, And Clinical Decision Support (STACDS) system. The STACDS system is configured to execute several methods independently or any combination of the methods. Embodiments may implement methods of machine learning-based predictive models and/or time series probabilistic clinical decision support algorithms. These algorithms may communicate and function separately or in tandem to forecast and/or control treatment variable value and parameters of interest by optimizing the clinical decision making process. Some embodiments of STACDS are also configured to execute performance management methods.

Figure 9:
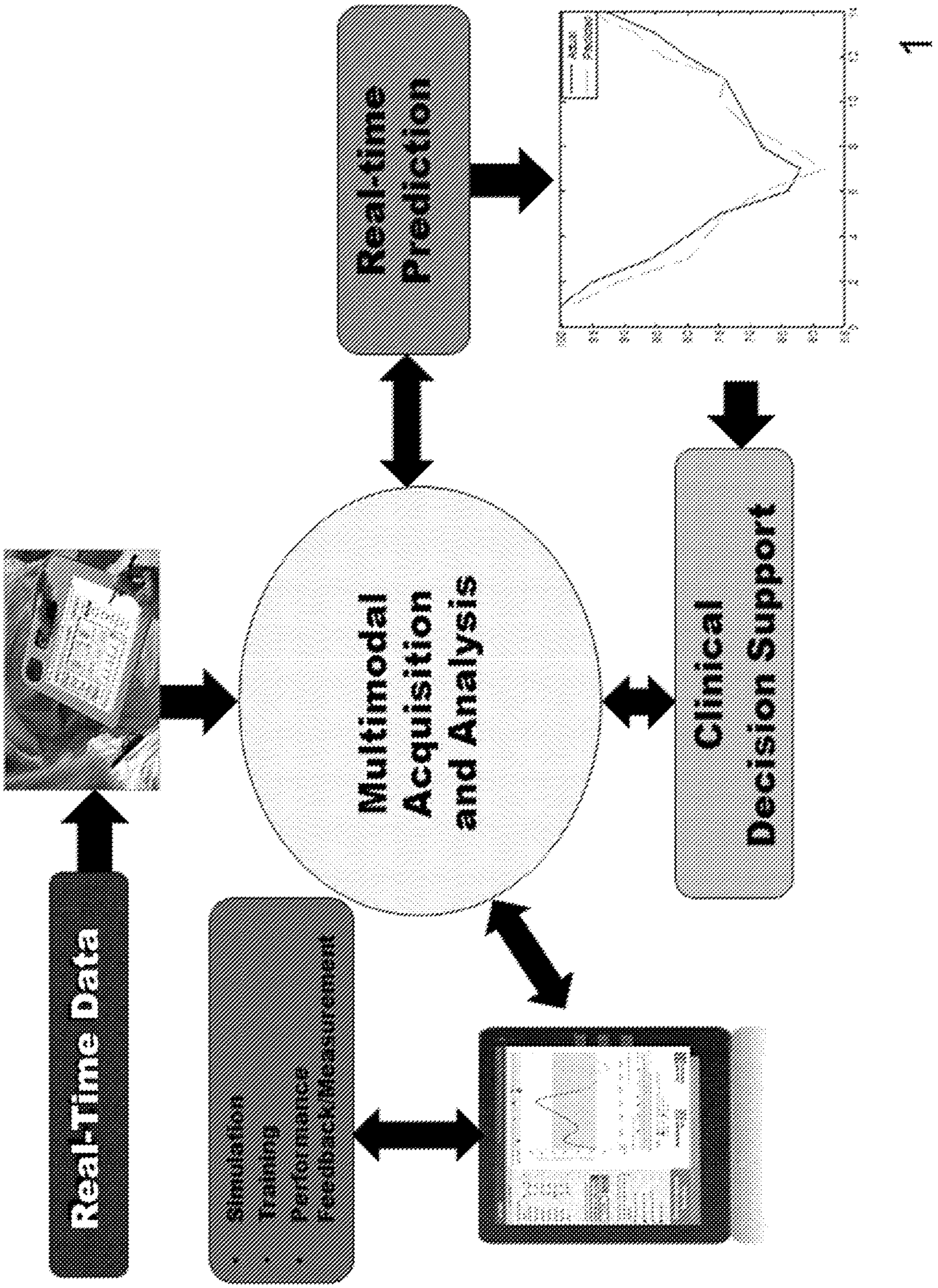
FIG. 9 illustrates a general functional architecture of one example embodiment of methods for clinical decision support.

A functional architecture of the STACDS methods consists of the three general methods including methods to provide: 1) measurement and assessment, 2) analytics, 3) clinical decision support. These methods include presenting the output of these methods through a user interface (UI) and also include methods to utilize the system with historical or simulated data for use in simulation and training. These methods are configured to function and communicate with each other to ensure STACDS' functionality and utility in supporting simulation, training, and clinical decision support. FIG. 9 demonstrates the interconnectivity of these functions, as performed by systems components, and the flow of data between them. Further description of these methods is included below.

The system may also be designed to serve as a closed-loop or semi-closed loop control system via integrating system output with a medication infusion device for example. In some embodiments suggestions derived from the decision support system can be sent to an insulin infusion device to change insulin dosages in real-time and not require the patient to interact with any of the devices. As a semi-closed loop solution, the user would still have to enter and accept suggestions made by the system which would then commit and make the changes to medication dosage for the patient/user.

Treatment Variables

Treatment variables, as input data to the methods of clinical support, may comprise any type of treatment data. Some embodiments of disclosed methods may be configured to integrate in real-time with any comprehensive EMR database, medical devices, and observer and/or self-reported measures. For example, treatment variables may comprise data as treatment variables from any number of physiological monitors or other data sources. Treatment variables may comprise any type of variable associated with the treatment or diagnosis of a subject such as, but not limited to analyte data, an intervention, a treatment data, a physiological data, a therapeutic data, an emotional data, a lifestyle data, an observed data, a self-reported data, an EMR data, a personal health records (PHR) data, a nutrition data, a medication data and a nursing scale. Treatment variables may be provided as real-time, historical or as simulated data.

The type of treatment variables measured and assessed will be dependent upon the potential different embodiments of the clinical support system. Embodiments may be directed to different target/intended clinical settings. For example, embodiments to support glucose control may utilize different data than embodiment of STACDS used to support pain management or an embodiment of STACDS to support detecting/predicting hemorrhagic shock.

Real-time data may comprise any data deemed significant for supporting optimize healthcare delivery and clinical decision making. Real-time data may comprise data from physiological monitors and may also comprise observed or self-reported data. For example and not for limitation, real-time data may comprise sensor data such as: data collected from patient vital signs monitors; data collected from other neural/physiological monitors; IV drips and drug infusion monitors; analyte level monitors; nutritional intake monitors (e.g., TPN, Enteral Tube Feeding, regular food by mouth, no food by mouth (NPO)) or any other type of clinical sensor monitoring the real-time physiological state of a subject. Real-time data may also comprise EMR data if it is acquired and communicated in real-time or near real-time.

Real-time data may also include observed or self-reported data that may be significant for clinical support and clinical decision making. Observed or self-reported data may include data such as: pain levels or Richmond Agitation Sedation Scale (RASS) scores (i.e. subjective self-report values from patient and/or healthcare provider perspectives to document how much pain the patient is in and how sedated is the subject is (RASS)); nutritional intake (e.g., TPN, Enteral Tube Feeding, regular food by mouth, no food by mouth (NPO)); patient demographics such as weight, age, sex, height, etc.; preexisting conditions (e.g., diabetes, epilepsy, etc.); medications taken; and any data related to the self-management of the subject's condition.

Historical data may comprise any data deemed significant for clinical support and decision making that is not real-time. For example and not for limitation, historical data may comprise: electronic medical records (EMR) data; laboratory results related to the subject; historical analyte flowsheet information (e.g., blood glucose readings, insulin dosage, etc.); pain levels; RASS scores (how much pain the patient is in and how sedated is the subject is); nutritional intake (e.g., TPN, Enteral Tube Feeding, regular food by mouth, no food by mouth (NPO)); patient demographics such as weight, age, sex, height, etc.; preexisting conditions (e.g., diabetes, epilepsy, etc.); key clinical events (e.g. sepsis, cardiac arrest, etc.), medications taken; or data related to the self-management of the subject's condition. Historical data may also comprise stored real-time data.

Real-time or historical data may also comprise lifestyle data such as but not limited to: sleep-wake cycles; sleep quality; exercise routines; day to day activities (e.g., housework, working at your job, etc.) of the subject; and emotional states of the subject such as but not limited to stress and depression.

Referring to FIG. 1A, treatment variables 110 to the measurement and assessment methods 130 may also include variables from other methods within the system. In some embodiments, input into the measurement and assessment methods 130 may also comprise results from the analyze methods 150 such as predictions that are generated by the predictive model(s) 152 of the end-solution or trends/patterns resulting from the methods to identify trends/patterns 156. In some embodiments, input into the measurement and assessment methods 130 may comprise interventions made by the user such as medication dosages, lifestyle changes, etc. In some embodiments, input into the measurement and assessment methods may also comprise performance measures generated based on the ability of the user to meet target/therapeutic goals set within the system by themselves or their healthcare provider. In some embodiments, input into the measurement and assessment methods may also comprise changes to current data "state" based on users use of the system for "what if" simulation/training functionality. This can include changing medication dosages for example to make values fall within the target range.

Measurement and Assessment Methods

Referring to FIG. 1A, the measurement and assessment methods 130 generally receive treatment variables 110, measure/interpret them, such as providing values to the treatment variables, and perform selected assessments on these variables. As shown, the measurement and assessment methods may comprise determining variable values at 132 and determining a performance measure at 140. These measurement and assessment methods 130 are configured to accept data as treatment variables 110 from any number of physiological monitors and data sources. Embodiments of the measurement and assessment methods may take input from subjects in either an inpatient setting where much of the input comes from medical sensors or hospital staff or in an outpatient setting where much of the input is entered by the subject or from sensors and medical monitors typical in an outpatient setting. For example, real-time data acquired from available physiological monitors may be processed and received as input by the measurement and assessment layer. Further, these methods may provide communication functions with other components of the system architecture (e.g., submitting real-time predictions to the UI or decision support methods).

Figure 1B:
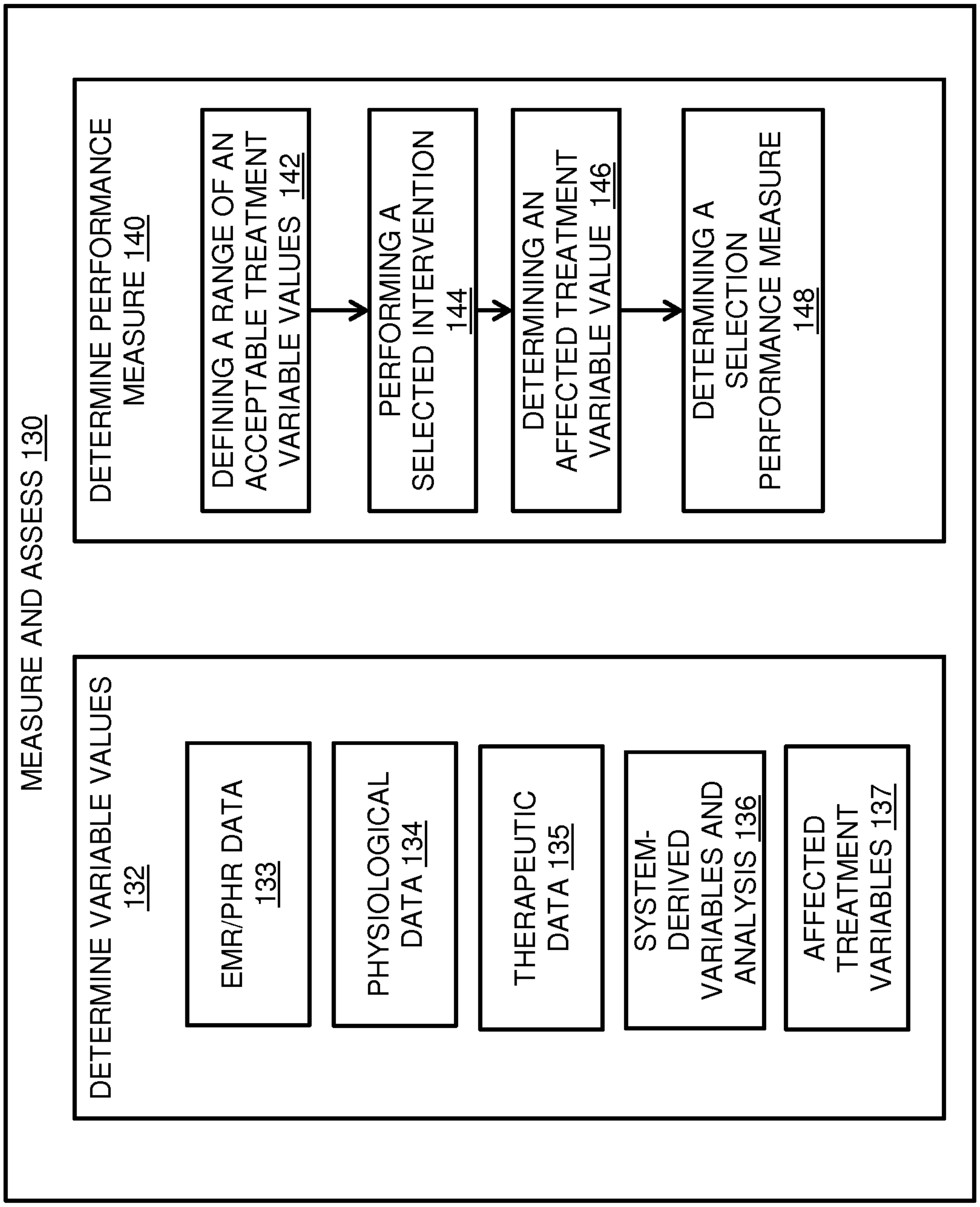
FIG. 1B illustrates a process diagram of one example embodiment of measurement and assessment methods.

FIG. 1B illustrates one example embodiment of the measurement and assessment methods 130. At 132, the methods measure variable data including but not limited to EMR/PHR data 133, physiological data 134, therapeutic data 135, therapeutic decisions/interventions, affected treatment variable 137, and system-derived variables and analysis 136 and determine the values of the variables. Also shown, the measurement and assessment methods 130 may include methods to measure the performance of users, here determining a performance measure 140. Determining a performance measure of users of the clinical support system may comprise any method of or system capable of comparing multiple sets of data from the clinical support systems and in order to measure and assess the performance of a user in meeting treatment/therapeutic goals. For example, the methods to determine a performance measure of users may comprise a method of comparing the outcomes of user-defined interventions (when they go against system decision support algorithm-generated recommendations) to expected outcomes of system decision support algorithm-generated interventions. The methods may also may compare the selection of interventions as the performance of a user to recommended interventions. Performance measurement is not necessarily a grade on the intervention but rather a grade on the overall ability of the user to meet goals of therapy over the course of time such as a particular patient's stay in the hospital (e.g. keep glucose values within the target range). The performance measures and scores generated from the methods are designed to be correlated with patient outcomes and therapeutic indicators indicating patient outcomes (e.g. higher scores will indicate better control in treatment variables, reduced morbidities/mortalities, etc.).

As shown in FIG. 1B, the methods to measure and assess the performance of users may be provided by determining a performance measure through a performance assessment at 140. Generally, one example embodiment of performance assessment comprises defining a range of acceptable treatment variable values for a treatment variable of a subject at 142, performing a selected intervention at 144, determining an affected treatment variable value after performing the selected intervention at 146 and automatically determining a selection performance measure at 148. In some embodiments, the selection performance measure comprises the clinical performance measurement of the selected intervention and this is determined by comparing the affected treatment variable value to the acceptable treatment variable values. Some embodiments further comprise defining a recommended intervention and automatically determining the selection performance measure as the clinical performance measurement of the selected intervention by comparing the affected treatment variable value to the acceptable treatment variable values and comparing the recommended intervention to the selected intervention. Some embodiments comprise an adaptive performance measure algorithm that adjusts its determination based on the user's ability to maintain treatment variables within acceptable ranges.

The performance assessment may be determined by a performance measurement algorithm which may be viewed as in an example embodiment and instantiation of a performance measurement and assessment algorithm, a state machine based system to calculate performance over time. The performance measure is dependent upon a variety of factors which surround the ability of the user to meet or exceed goals of therapy (for diabetic patients this would be to maintain glucose values within a target range). The performance measurement algorithm may provide measures of performance which will take into account a variety of factors such as but not limited to: ability to maintain the treatment variable values such as physiological/therapeutic values within a user-defined, healthcare provider-defined, or gold-standard target range, the number of patient treatment/lifestyle decisions leading to desirable glycemic control, maintaining a desirable frequency of monitoring, and overall use of the system features to better improve knowledge of their disease and disease-related problem solving and decision making. For example, in the case of a subject with diabetes, the number of subject's decisions made in-line with recommendations suggested by the decision support algorithms leading to desirable outcomes (e.g. better glycemic control) will result in increased performance scores. Conversely, contradicting system suggestions which lead to adverse outcomes (e.g. low or high BG values) will result in decreased performance measure scores. The performance measurement algorithm output (on a 0-100 scale) may be correlated with gold-standard indicators of patient outcome (for patients with diabetes this is maintenance of glycemic control within a target range (time spent in target range), and other therapeutic indicators such as glycated hemoglobin A1C (HbA1C)). When implemented, performance may be defined to begin with a performance measurement of 100 at system use, and the decisions the user makes in terms of therapy (medication dosages for example) will result in increases or decreases in performance measure. The performance measure will be different based on end-target patient population and application.

In one example embodiment of a performance measurement algorithm, the results of the algorithm provide a means to numerically quantify the performance of the user in maintaining desirable patient/healthcare outcomes. In this embodiment, the performance measure is not quantified as good or bad but rather it is to be quantified on a finite and quantifiable scale (e.g. 0-100). In some embodiment, the measures may be provided dynamically and adjust this performance measure in real-time. The real-time feedback provided by the performance measurement and assessment will provided users an indicator of how well they are meeting their treatment goals, and in the short and long term avoiding adverse health outcomes such as increased morbidities, mortality, incidence of complications, etc. The case identified below is one example way of calculating these performance measures dynamically on a second by second or minute by minute basis. In one example embodiment, the performance measurement algorithm dynamically calculates performance on a finite scale (e.g. 0-100). Performance initially begins at the maximum value of the finite scale (e.g. 100 on a 0 to 100 scale) This performance measure is modified/adjusted based on numerically quantifying changes the user's decision making as it relates to facilitating optimal patient/healthcare outcomes, and maintaining treatment variables within a target range. The performance measure is adjusted based on number of potential factors such as but not limited to (1) the amount of time spent within and outside a target range of values over predefined and/or configurable windows in time and (2) the overall decision making capabilities of the user. As an example of adjusting performance based on the amount of time spent within and outside a target range of values over predefined and/or configurable windows in time, performance is increased or decreased by a constant value k*N where k is a positive value greater than zero and N is the number of consecutive values within or outside of the target range. In this case performance is increased the more the treatment variable in maintained within the target range. Conversely performance decreases the more the treatment variable falls outside of the target range. As an example of adjusting the performance measure based on numerically quantifying the overall decision making capabilities of the user, the decision making of the user can be evaluated based on their overall ability to recognize when the suggestions generated by the decision support capabilities of the system are accurate, and when there is need to deviate from these suggestions. For example, if the user accepts a suggestion for an intervention (e.g. increase basal insulin infusion rate to 3.5 U/hr) made by the system and this leads to a favorable outcome (i.e. maintenance of a treatment variable within a target range) the system generated performance measure (on a finite scale) will be increased. Conversely, if the user chooses to not accept recommendations generated by the system and this leads to an adverse outcome (i.e. treatment variable exceeds target range for an extended period in time), the system performance measure will be decreased. The performance measure will be adjusted based on the methods as outlined above. In an example case, performance is increased or decreased by a constant value k*N where k is a positive value greater than zero and N is the number of consecutive decisions leading to desirable or undesirable outcomes (e.g. treatment variable falling within or outside of target range). As above, performance is increased the more decisions lead to the treatment variable being maintained within the target range. Conversely performance decreases the more user decisions cause the treatment variable to fall outside of the target range. As another example when treatment variables are collected on a continuous basis second by second or minute by minute for example, performance can be adjusted based on the percentage of time $t_p$ (over a predefined or configurable time window) spent within or outside of a target range. In this case, the larger the percentage of time (maximum value=100%), the more performance is increased or decreased. Thus the current system performance measure P(t) is adjusted based on adding some constant k scaled by $t_p$ to the current performance measure (i.e. $P(t)=P(t)+k*t_p$).

In some embodiments in a real-time environment, the performance will be measured in real-time continuously and this will change dynamically. The user will have the option to select a view of performance over time, as well as to identify periods in time where performance was degraded or optimal (and point to possible reasons why).

In some embodiments, measures from performance assessments may be used to support reimbursement for services in the implementation of the Affordable Care Act (Obama Care). Performance measures may also help user identify staffing requirements needed to optimize care and minimize costs to a healthcare institution. For example, healthcare administrators could identify through analysis of system-generated performance measures that only a staff of 3 nurses rather than six are needed for night shift and that patient care and quality does not reduce given reduction of nursing staff.

Performance assessments may be used to evaluate the performance of staff/patients in terms of decision-making and problem solving (i.e. being able to identify when to use or deviate from suggestions generated by clinical decision support system, and using other functionality of decision support system to lead to optimal decision)

Some embodiments of performance assessments may provide retrospective and real-time assessments of performance and identification of time domains where performance is good or poor (coupled with the pattern recognition and other algorithms and predictive analytics in system). Users can use this information in combination with predictive models, decision support models, and pattern recognition and other information available by the system to identify reasons why performance is favorable or poor. In outpatient embodiments (e.g., patients with diabetes) the patient can determine which lifestyle or treatment decisions cause undesirable changes in performance for example. In the inpatient setting, hospital administrators (for example) can use this information to identify staffing issues (under staffing, or need to staff more senior employees, or improve transition between shift changes) to avoid decrements in performance and patient care. Retrospective analysis of historical performance data may also indicate need for changes in therapy, allocation of healthcare staff/resources, and need to modify existing institution drug delivery protocols.

In some embodiments, performance assessments may indicate the abilities of the patients/clinical staff to maintain treatment variable values within desired and user customizable target ranges, as well as the percentage of decisions aligned with the decisions suggested by a clinical decision support component. The system's performance measures (based on particular therapeutic goals) and real-time performance feedback is designed to have a high correlation with quality of health care, quality/success of patient/clinical staff-directed therapies, clinical/patient outcomes, appropriate allocation and skill set of healthcare staff, as well as optimal clinical decision making and understanding of specific therapies (from a training/educational perspective).

In some embodiments, performance assessments of the disclosed systems and methods may be derived to be highly correlated with literature-based relationships which are defined for maintaining treatment variable values within (literature defined) target ranges. The user however, will have the ability to customize the target ranges (from default values) for each treatment variables of interest.

Analytic Methods

Analytic methods for clinical support systems and methods may comprise any method to analyze the data received. The analytics methods of clinical support systems may implement different methods of analysis such as predictive methods, trend/pattern recognition methods and methods to "train" and "personalize" or improve the models implementing these methods.

Figure 1C:
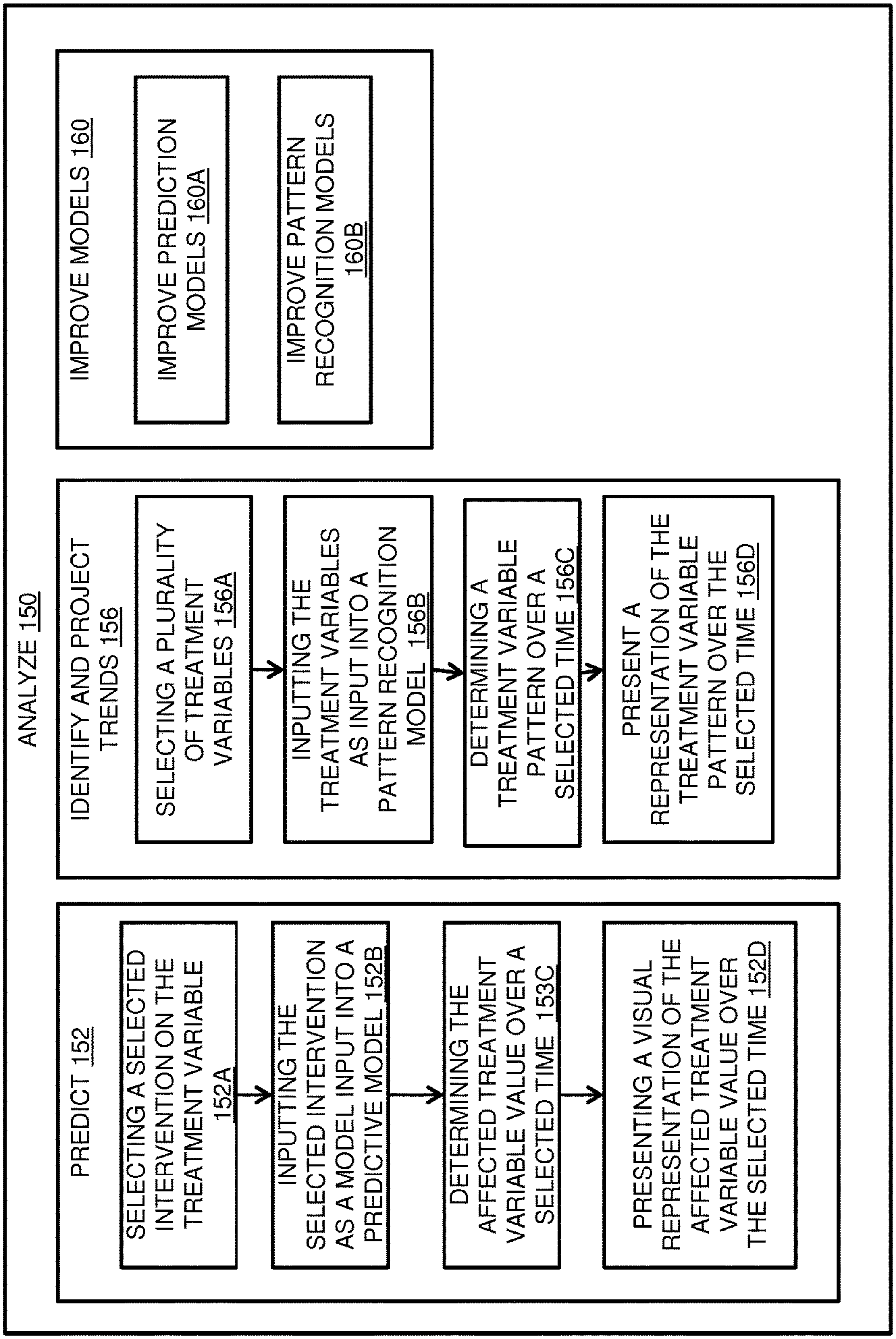
FIG. 1C illustrates a process diagram of one example embodiment of analytic methods.

FIG. 1C illustrates one example embodiment of methods for providing analytic methods 150. As shown, these analytic methods 150 may comprise predictive methods 152 or trend/pattern recognition methods to identify and project trends at 156.

As shown at 152, some embodiments of predictive methods comprise selecting a selected intervention on the treatment variable at 152A, inputting the selected intervention as a model input into a predictive model at 152B and determining the affected treatment variable value over a selected time by modeling the selected intervention on the treatment variable over the selected time at 152C. Some embodiments present a representation of the affected treatment variable value over the selected time at 152D. In some embodiments, the predictive methods are provided by predictive models (e.g., machine learning-based) that forecast and predict data such as physiological and therapeutic measures and other levels of interest. Model input and model predictive results may also be used to simulate physiological responses based on user specified interventions. In some embodiments, the prediction models are adaptive (can learn trends specific to only single patients and certain patient cohorts), can take into account multiple inputs simultaneously, and output a continuous vector or trajectory of predicted values across a predefined or selectable prediction horizon. For example, suitable models may include various types of machine learning algorithms, neural networks, probabilistic models, and other models with linear and non-linear predictive functionality. In some embodiments, the predictive methods may be configured to predict future changes in the different treatment variables (for each organ system cardiac, renal, endocrine, respiratory, neurological, etc) based on continuous changes in patient EMR and decisions/interventions made by clinical staff. This has been investigated using a neural network based approach as they are well-suited to account for the effect of any number of input variables and features, can adapt to an individual patient over time based on new incoming EMR and physiological responses, and can be utilized to simulate the effect of one or multiple changes in interventions on any given set point of interest. In some embodiments, the predictive model comprises a machine learning algorithm. In some embodiments, the machine learning-based predictive model comprises a neural network.

In some embodiments, a suitable method to predict data comprises methods similar to those described in U.S. Pub. No. 2011/0225112 of U.S. patent application Ser. No. 13/058,673 to Brent D. Cameron et al., filed on Aug. 14, 2009 and published on Sep. 15, 2011 which is herein incorporated by reference in its entirety. In some embodiments, a suitable method to predict data comprises methods similar to those described in U.S. Pub. No. 2010/0292634 of U.S. patent application Ser. No. 12/305,582 to Robert C. Kircher, JR. et al., filed on Jun. 19, 2007 and published on Nov. 18, 2010 which is herein incorporated by reference in its entirety. These embodiments are particularly suitable for predicting glucose levels in patients.

As shown in FIG. 1C, the analytic methods 150 may implement augmented visualization of EMR, medical device, and other clinical/medical data via implementation of pattern recognition algorithms (combination of unsupervised and semi-supervised algorithms) to identify and project patterns or trends in treatment variable values of interest at 156. Pattern recognition can be implemented using pattern recognition algorithms. For example, a stochastic search algorithm can be implemented to find patterns existent in comprehensive medical records or similar datasets. Using this embodiment, physicians/patients can identify possible future trends in these values within similar patients (or themselves in the patient-centered solution).

As shown in FIG. 1C, some embodiments of trend/pattern recognition methods at 156 may comprise selecting a plurality of treatment variables at 156A, inputting the treatment variables as input into a pattern recognition model at 156B and determining a treatment variable pattern over a selected time by recognizing the treatment variable pattern over the selected time at 156C. Some embodiments may present a representation of the treatment variable pattern over the selected time at 156D. For example, trend/pattern recognition methods 156 may also be used to forecast and predict data such as physiological and therapeutic measures and other levels of interest. Trends which we are interested in are reproducible patterns in data which occur in similar patient types (patients with diabetes with similar demographics). Trends and patterns in data can identify when values are most likely going to outside of target range (high or low) based on the current real-time data being processed to uncover similar patterns and trends. For example only, one embodiment of identifying and utilizing trend data can comprise an Event-Centered Pattern Recognition Algorithm which identifies similar patterns and trends. For example in the case of glucose values, an Event Centric Pattern Recognition (ECPR) may be used to identify events from the subject's historical data to predict and identify patterns and trends in future glucose values. The subject's current state, comprised of current/real-time data collected will be matched with events via a hybrid case-based reasoning pattern recognition approach for estimating BG levels. As data is entered into the clinical support system, historical data will provide the knowledge base for this pattern recognition feature. The subject's current data will be compared against their historical data, and/or data from like subjects, to search for similar events in order to assign a similarity rating. Events exceeding a similarity rating threshold are then statistically analyzed to provide an estimation of future glucose trends (e.g. expectations for the next patient BG value e.g. low, high, and normal). As historical data grows with continued use of these methods, the number of events exceeding the similarity threshold will increase and produce case-based estimations with higher levels of confidence and accuracy.

In some embodiments, a suitable method for trend/pattern recognition comprises methods similar to those described in W.I.P.O. Pub. No. WO2013/126144 of Int. App. No. PCT/US12/72313 to Aptima, Inc. et al, filed on Dec. 31, 2012 and published on Aug. 29, 2013 which is herein incorporated by reference in its entirety.

Some embodiments of analytic methods comprise identifying a treatment indicator by performing a pattern recognition analysis on the plurality of affected treatment variable values whereby the treatment indicator associates the selected intervention with one of a good affected treatment variable value or a bad affected treatment variable value (i.e. identification and analysis whether the target treatment variable is outside (bad) or within (good) target range). Some embodiments of analytic methods comprise identifying a performance indicator by performing a pattern recognition analysis on the plurality of selected performance measures whereby the performance indicator associates the selected intervention with one of a favorable (good performance measure) or unfavorable (poor performance measure) healthcare related and patient outcomes.

In some embodiments, the analytic methods provide both short term (75 minutes ahead) and long term (>24 hours) prediction and identification of trends/patterns in glucose and other related electronic medical records (EMR) data.

As shown in FIG. 1C at 160, some embodiments of analytic methods 150 further comprise improving the models used in those analytic methods at 160. Embodiments may improve the prediction models at 160A or improve the pattern recognition models at 160B. For example, improving models may comprise using the machine learning algorithms in real-time and adapting their weights dynamically given acquisition of more data for a specific patient or group of patients as the system is used. A comprehensive data set of all data used by the models can be used to retrain the models such that accuracy is improved. For example, in an example embodiment for patients in the hospital with lack of glucose control, the models initially used for prediction of glucose and decision support may be based off of treatment variable data collected from a number of patients. While the patient maintains their stay in the hospital, a large quantity of treatment variable data can be collected and used to "retrain" and adapt model weights to provide better accuracy for a specific patient. The accuracy may increase when the dataset used to improve and retrain the model becomes comprised more of the treatment variable data from the current patient rather than comprised of a variety of patients. This may make the model more personalized and patient specific.

Some embodiments of the analytic methods 150 further comprise receiving a plurality of treatment variable values for the treatment variable over a treatment time period, each of the treatment variable values associated with one or more time in the treatment time period and storing the treatment variable values associated with one or more time in the treatment time period whereby the plurality of treatment variables may be played back as associated with the one or more time in the reporting time period.

These analytic methods may be used in real-time as EMR and PHR data is collected in real-time as well as retrospectively using historical or simulated data. The analytics methods may be designed to predict the effect of the patient's/subject's current state (comprised of all available data sources) for a complete vector/trajectory of "treatment variable" values across a configurable prediction horizon.

Clinical Decision Support Methods

Clinical decision support methods may comprise any method of providing additional data to a user such that they may be more informed to make better decision for the subject. Some embodiments of systems and methods for clinical support may allow the caregiver to "experiment", to simulate the effect of treatments or interventions, based on current and historical patient states.

Figure 1D:
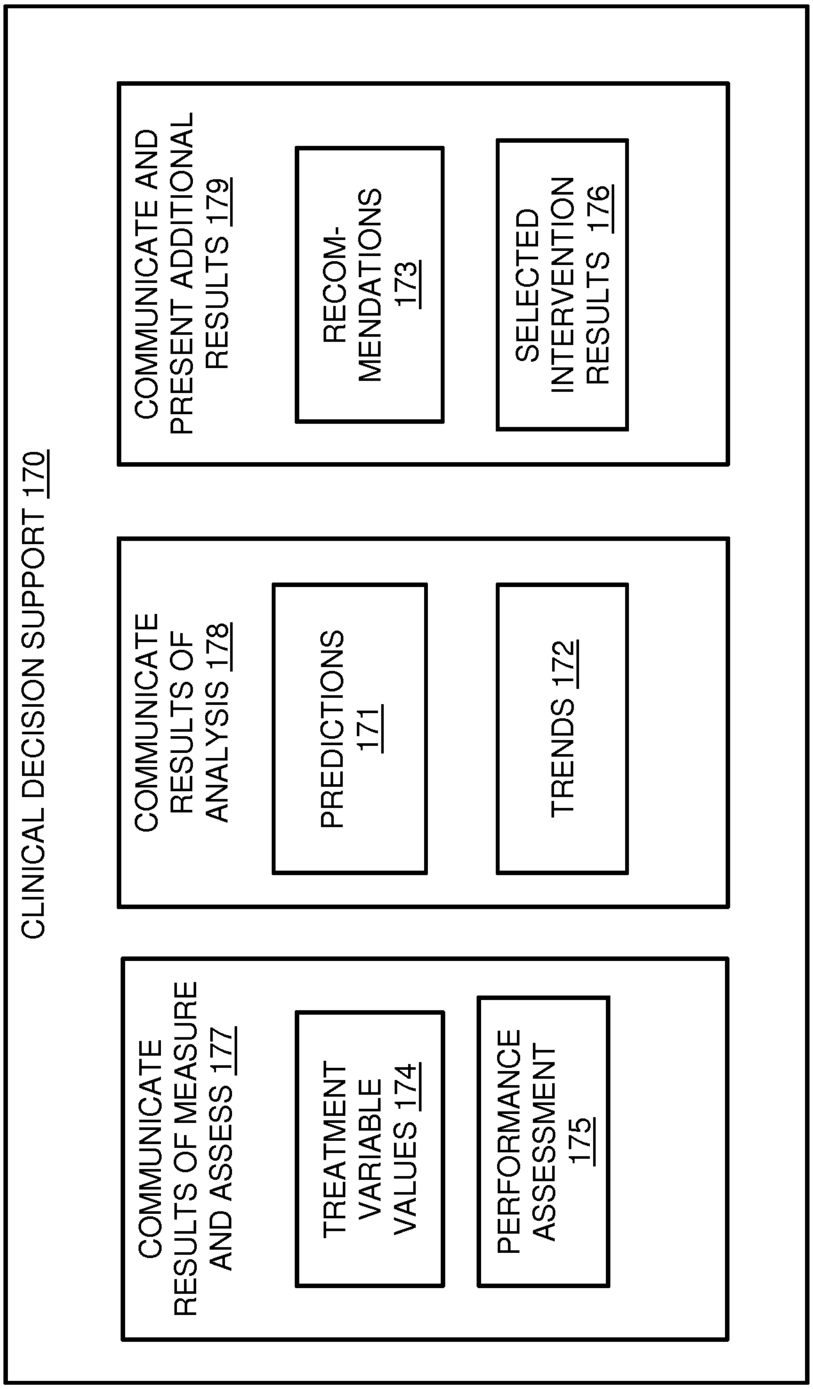
FIG. 1D illustrates a process diagram of one example embodiment of decision support methods.

FIG. 1D illustrates one example embodiment of methods 170 for providing clinical decision support. As shown, clinical decision support may be provided through different methods such as communicating the results of the measure and assess methods at 177, communicating the results of the analysis methods at 178 or communicating and presenting additional results at 179. Communicating the results of measure and assess methods at 177 may comprise communicating treatment variable 174 and performance assessment 175. Communicating the results of analysis methods at 178 may comprise communicating predictions 171 and communicating trends 172. Communicating and presenting additional results at 179 may comprise communicating recommendations 173 and selected intervention results 176.

Some embodiments of clinical decision support methods may also comprise presenting a visual representation of at least one additional treatment variable value. In some embodiments, the additional treatment variable is selected from the group consisting of: a treatment data; an emotional data; a lifestyle data; an observed data; a self-reported data; an electronic medical record (EMR) data; a personal health records (PHR) data; a nutrition data; a medication data; and a nursing scale.

Some embodiments further comprise automatically determining a recommended intervention as the selected intervention before performing the selected intervention. In some embodiments, automatically determining a recommended intervention as the selected intervention comprises automatically determining a recommend intervention as the selected intervention utilizing a Partially Observable Markov Decision Process (POMDP) algorithm to model the affected treatment variable value.

Some embodiments further comprise, before performing the selected intervention on the treatment variable, selecting a selected intervention on the treatment variable, inputting the selected intervention as a model input into a predictive model, determining the affected treatment variable value over a selected time by modeling the selected intervention on the treatment variable over the selected time and presenting a visual representation of the affected treatment variable value over the selected time.

In some embodiments, the decision support methods provide subject intervention recommendations to help maintain physiological and therapeutic values of interest within target ranges specified by healthcare personnel. For example, the clinical decision support methods may suggest what medications, decisions, or interventions to implement. In some embodiments, clinical staff may choose to implement or to ignore these recommendations and their choice may be logged in a database for further evaluation. One embodiment utilizes a Partially Observable Markov Decision Process (POMDP) algorithm for decision support. This time series, probabilistic modeling approach leverages information from real-time and historical trends in physiological signals as well as predictive measures (derived from the prediction layer) to estimate patient state and recommend an optimal course of action. The methods his may also include extended Hidden Markov Models (HMM) or other algorithms for clinical decision support as well.

In alternate embodiments, model predictive control algorithms or other control systems algorithms can be implemented as well. For one embodiment of the clinical decision support algorithm comprises a POMDP. This has demonstrated initial success however other model other modalities such as POMDP/Hidden Markov model hybrid models, model predictive control algorithms, and even machine learning algorithms could also be used. One approach to mathematically modeling the patient treatment process is to combine multiple sources of observable information to hypothesize about non-observable information and produce an optimized action plan (policy) using a POMDP. The observable information sources may include the patient's current physiological signals, EMR data indicative of patient treatment and health status, as well as predictive results given by the analytic methods described herein. Once a policy is obtained it will be used iteratively to obtain real-time treatment recommendations individualized for each patient based on their response to the treatment that is being administered. Once the POMDP is generated it basically can function as a "lookup table" which is important as it can be efficiently executed even on resource constrained mobile platforms.

In some embodiments, POMDP/HMM can be used in tandem to identify state transitions (HMM), and determine (based on the current state and real-time data) the optimal intervention (medication dosage, lifestyle change, etc.) which will lead to the best outcome (maintenance of the treatment variable value within the target range).

In some embodiments, a suitable means for clinical decision support comprises utilizing methods and algorithms similar to those described in U.S. Pub. No. US2011/0016967 of U.S. application Ser. No. 12/921,755 to Georgiy Levchuk et al, having a 371(c)(1), (2), (4) date of Sep. 9, 2010 and published on Jan. 20, 2011 which is herein incorporated by reference in its entirety.

In some embodiments, conventional control system models/algorithms such as model predictive control, proportional-integral-derivative (PID) controllers, and others can be implemented to determine optimal medication dosages.

The decision support methods may be available prior to selecting an intervention and they may be available after the intervention.

The decision support methods may provide decision support reflecting the prediction of an intervention.

User Interface

Figure 2A:
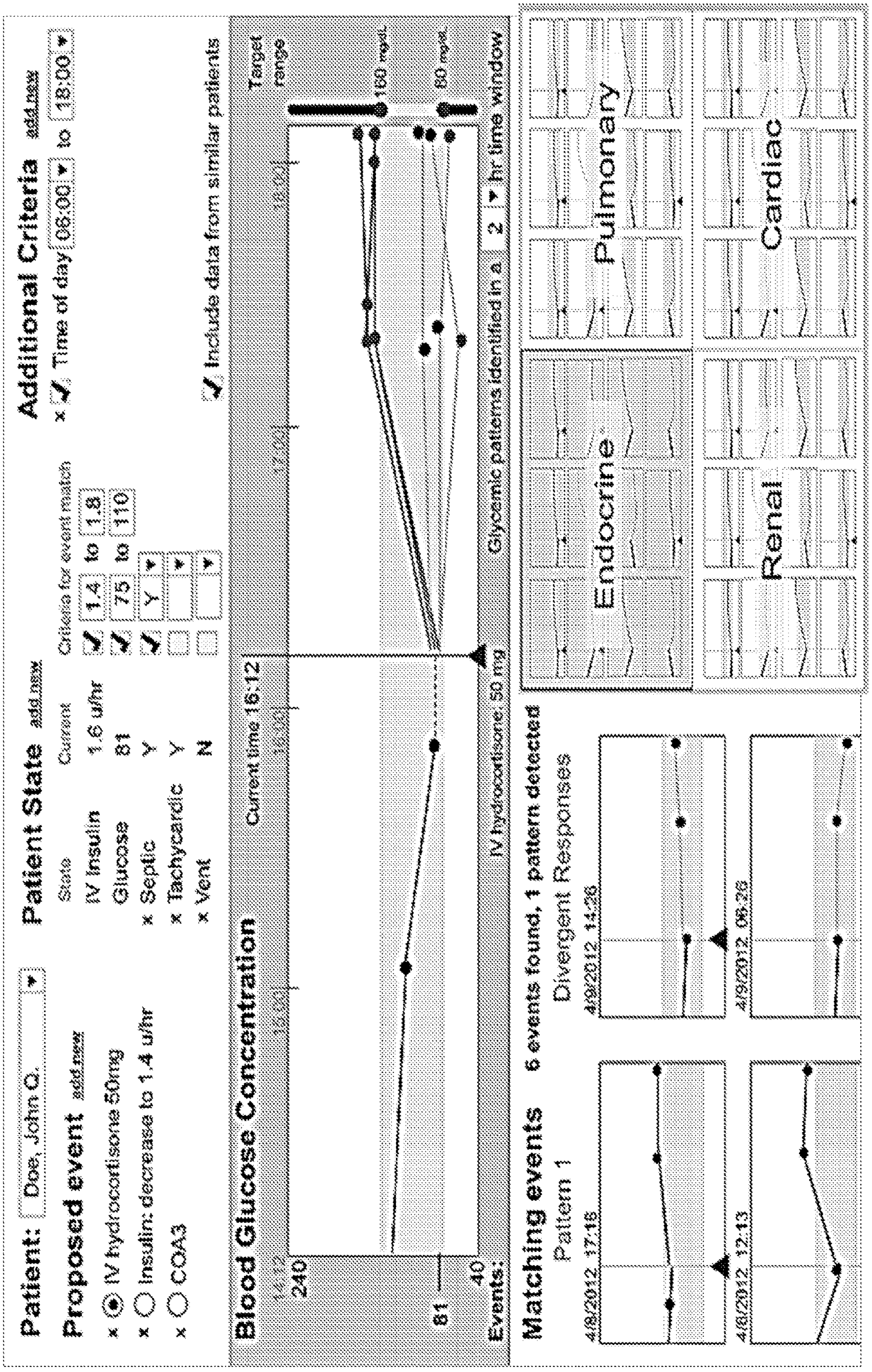
FIG. 2A illustrates one example user interface design.
Figure 2B:
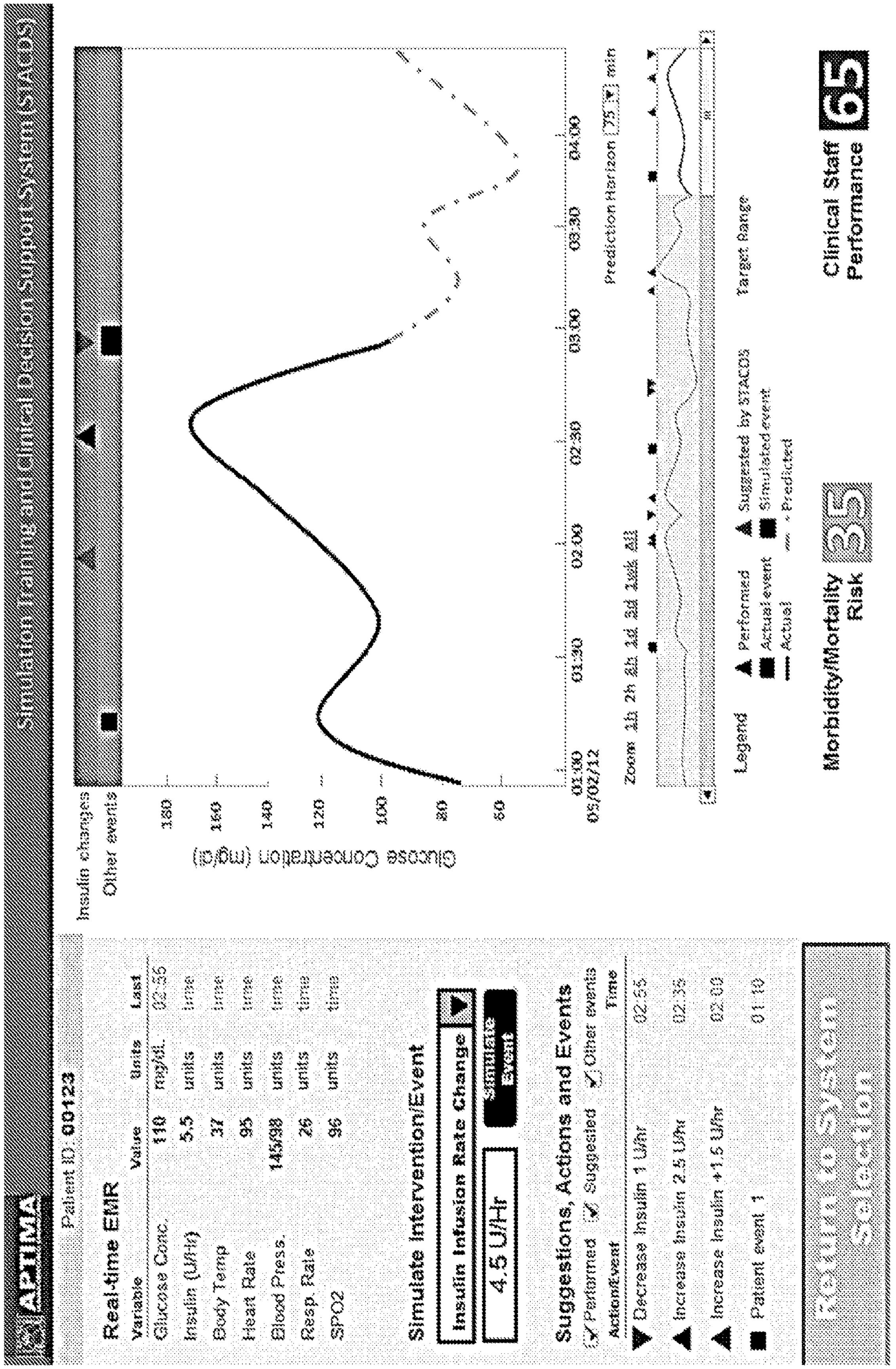
FIG. 2B illustrates another example user interface design.
Figure 2C:
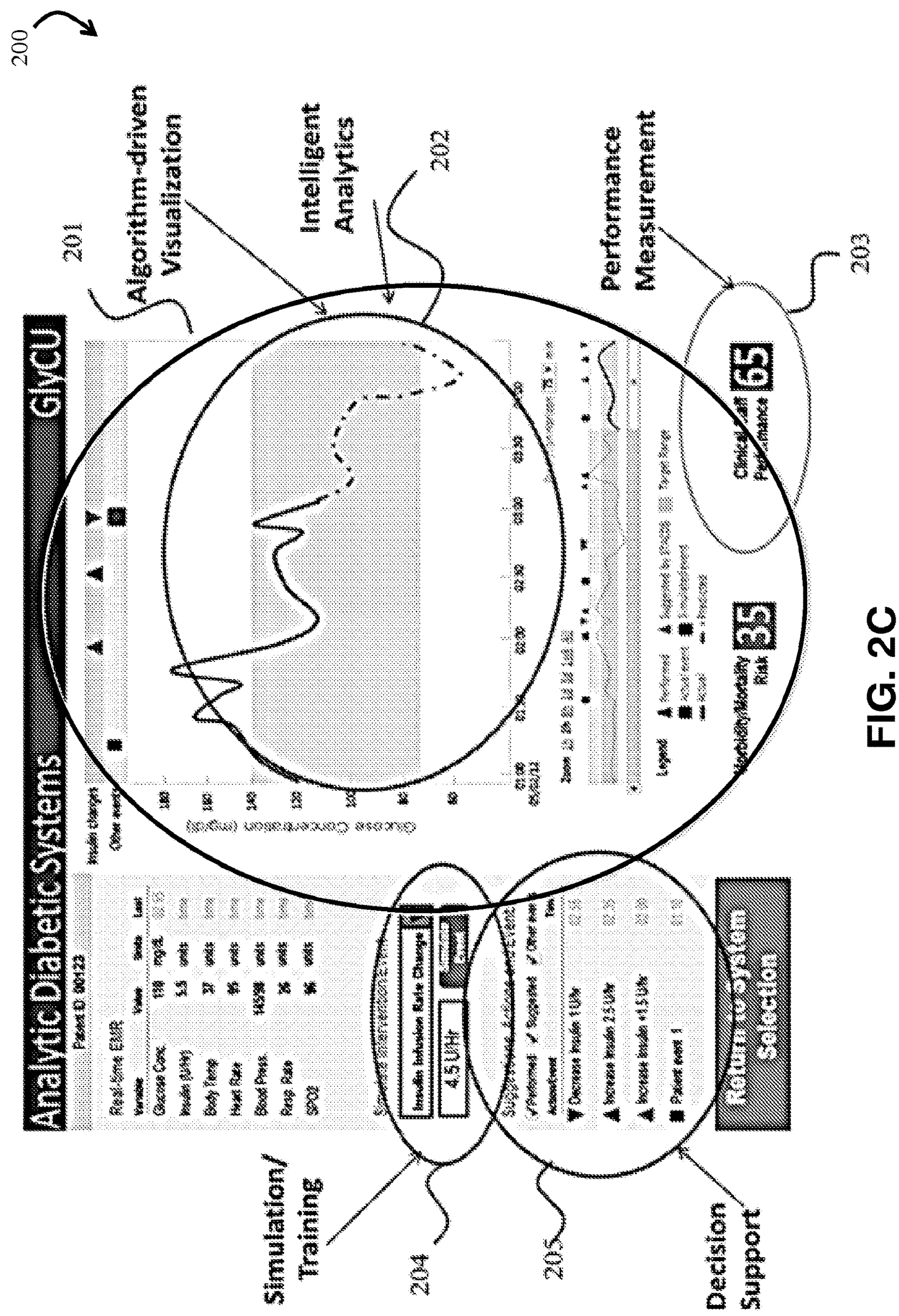
FIG. 2C illustrates another example user interface design.

Means to present output from the clinical support systems may comprise presenting output through any a user interface or any other method of communicating output to a user. For example and not for limitation, means to present output may comprise user interfaces such as a computer monitor, graphic interface, audio interface or any other user interface. FIGS. 2A-2C illustrate example embodiments of user interfaces suitable for use with the disclosed clinical support systems.

In some embodiments, the clinical support system user interface may provide the user with performance measurement data, clinical support data and simulation and training data. The user interface may provide performance measurement feedback to the medical staff on effectiveness of care and their ability to maintain therapeutic goals. Trends in physiological data, predicted responses, and decision recommendations may be presented to optimize the clinical decision making process and patient outcomes. The user interface may support simulation and training in either real-time or retrospective modes. Retrospective modes of the clinical support methods may include the ability to load historical subject records and allow the user to simulate interventions and clinical decisions to gauge and improve performance in maintaining appropriate patient state.

The user interface may optimize the fit between the domain expertise of medical personnel and advanced automation. The interface may be optimized and guided by human factors engineers and input from subject matter experts (SMEs) and end-users (medical personnel (nurses, physicians, etc.)) from target healthcare environments and settings to: (1) simplify the medical personnel's interaction with the output of the clinical support system's complex models and algorithms instituted in the real-time prediction and clinical decision support layers (2) reduce cognitive overload by applying human factors design principles to intelligently layer information to deliver the most critical information at a given time; (3) offer intelligent decision support by recommending treatment strategies and providing feedback on past decisions; (4) allow the medical staff to explore alternative medical therapies through "what-if" simulations; and (5) enhance a medical staff's ability to manage multiple subject by enabling seamless transitions from high-level multi-subject views and more detailed subject data.

FIG. 2B illustrates an example user interface for an implementation of clinical support systems to support optimization of inpatient glycemic control. In this embodiment, the clinical support system is configured to communicate with a continuous glucose monitoring device which provides measurement of interstitial glucose concentration every 5 minutes (although discrete point of care blood glucose monitoring results can also be the main source of data). In this embodiment, medical personnel are provided views of real-time electronics medical records data, historical and current glucose monitoring data, and predicted trends in glucose data (provided by the prediction layer). Additionally, the medical staff is provided real-time performance measures as feedback on a 0-100 scale. This performance measure is provided by an algorithm which is based on their ability to maintain target treatment variable values (glucose in this case) within medical staff or healthcare institution customizable target ranges. The performance measure also takes into account the percentage of the clinical decisions which were in-line with clinical support systems recommendations (generated by the clinical decision support layer) or user-specified interventions which lead to desirable outcomes. The user can click on the performance measurement indicator to present historical performance data over time. This may provide healthcare institutions, medical staff, insurance companies, auditors, and other key personnel insight which will support allocation of resources, staff, effectiveness of therapeutic protocols, and other information which will allow further optimization of patient care. Also within the user interface, medical staff may be provided with an indicator of mortality and morbidity which is derived based on how successful medical personnel are in maintaining treatment variable value within literature and institution specified target ranges for optimal patient care. In outpatient embodiments this can be associated with different patient outcome indicators such as for example risk of cardiovascular disease, glycated hemoglobin HbA1C values, and diabetes complications. Another feature illustrated with this interface is ability of the clinical support system to simulate the effects of interventions before they are implemented. In the case of the embodiment demonstrated in FIG. 2B, medical personnel can simulate the effect of giving changing medication dosages (e.g. insulin infusion rate) to gauge the overall effect on the treatment variable of interest. In FIG. 2B, the user increases insulin infusion rate which causes undesirable low glucose values. Using STACDS simulation capabilities, the medical personnel can then experiment with different interventions to optimize decision making and consequently patient outcome. Additionally, this capability can also provide real-time learning/training on how specific interventions, medications, and other changes in patient state interact with each other. Historical data can be loaded into the STACDS system to facilitate further utility in training via simulated real-time playback of prerecorded/collected patient data. Using historical data, the user can still experiment with "what if" simulations and other comprehensive system functionality as if they were actually treating the patient.

FIG. 2C illustrates the example user interface of FIG. 2B highlighting selected features of the user interface 200. As shown, user interface 200 contains an area showing algorithm-driven visualization 201 which presents different treatment variables in a visual way to the user. The interface also illustrates the results of intelligent analytics at 202. The interface 200 also shows performance measurement at 203. Here, performance measurement comprises a numeric grade of 65 out of a possible score of 100. The interface also shows decision support presented at 205. Here, decision support comprises a visual of selected treatment variables with graphic flag further describing the trend of the variable. The interface also comprises a simulation and training area 204. Here, the simulation and training area 204 allows a use to selected a simulated intervention which will be projected out and affected treatment variables will be displayed on the interface.

In some embodiments, the user interface may also provide alerts/alarms when treatment variable values or performance metrics exceed default and user-customizable target ranges, or when the system predictive layer predicts that they will exceed these ranges. In some embodiments, the disclosed clinical support systems and methods may be able to provide real-time alerts when patient/medical staff performance falls below (or is predicted below) desirable levels, and when performance may lead to adverse outcomes such as increased morbidity and mortality.

Simulation and Training Methods

In some embodiments, the systems and methods further comprise methods for simulation and training. In these embodiments, the methods are able to utilize simulated or historical data from the database 102 as treatment variables for the methods to use in the simulation. Utilizing these methods allow healthcare personnel and patients to explore how current and historical interventions and states affect treatment variable values and other key outcomes. In embodiments, the simulation and training methods are able to playback (in a simulated real-time setting) actual prerecord/pre-collected historical patient data. In some embodiments, the subject is a hypothetical subject, the acceptable treatment variable values are model treatment variable values of a clinical simulation and the clinical performance measurement is a simulated clinical performance measurement of a clinical training simulator. In some embodiments the subject is a hypothetical subject, the acceptable treatment variable values are model treatment variable values in a clinical simulation and the clinical performance measurement is a simulated clinical performance measurement of a clinical training simulator.

Some embodiments of clinical support methods are configured to training to system users. For example, some embodiments of the disclosed systems and methods may be loaded with treatment variables from a number of patients and utilized as a training environment. This can be used for enhanced clinical staff training and/or training of residents and medical students. Staff or students can be given characteristics of a particular patient and asked to monitor EMR and physiological data in a simulated real-time environment and commit to actual clinical decisions and interventions using the disclosed systems as a virtual patient-like training environment. The performance of the clinical staff will be an output from the performance assessment at the end of a training session on a continuous timeline as well as an overall score. Based on literature and known treatment outcomes, the performance measurement and assessment provided by the system will indicate whether the patient would have recovered successfully, had an increased hospital stay with morbidities, or died.

In another example, some embodiments may provide a simulation capability that patients/clinical staff can vary any data present in EMR prior to actually committing to a clinical decision to see the "predicted" effect on a certain treatment variables of interest. Because the pattern recognition and predictive models (intelligent processing and analytics) some embodiments may be trained with a significant source of data, the systems may be able to account for various patient groups with different characteristics which will have similar physiological responses to the interventions or clinical decisions.

Figure 3:
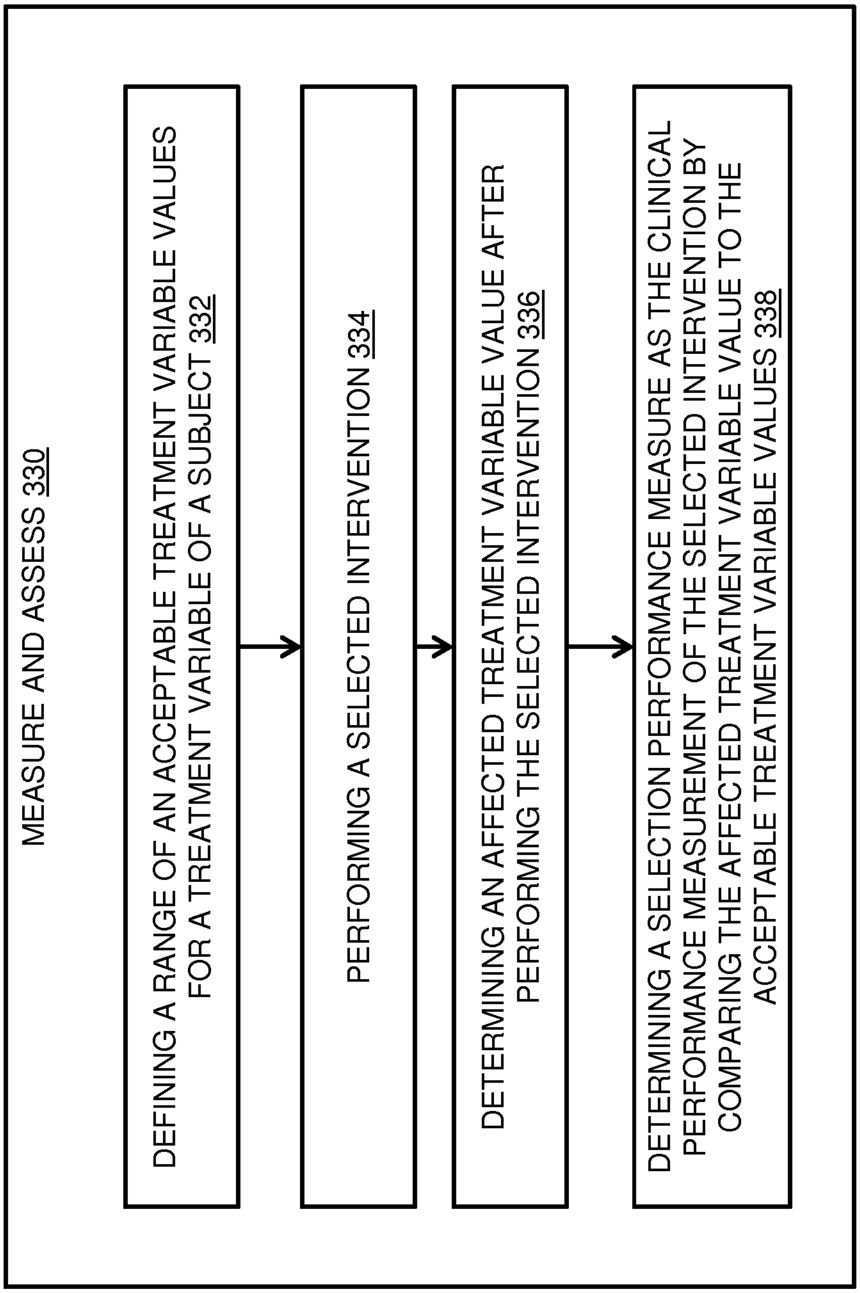
FIG. 3 illustrates a process diagram of one example embodiment of methods for clinical decision support.

An Example Embodiment of the Clinical Support Methods, Measurement and Assessment Methods Some embodiments of clinical support methods are configured to provide measurement and assessment methods to system users. As shown in FIG. 3, one example embodiment of measure and assess methods 330 comprises defining a range of an acceptable treatment variable values for a treatment variable of a subject at 332, performing a selected intervention at 334, determining an affected treatment variable value after performing the selected intervention at 336 and automatically determining a selection performance measure as the clinical performance measurement of the selected intervention by comparing the affected treatment variable value to the acceptable treatment variable values. In some embodiments, the performance measure comprises modifying the performance measure from a starting measure or from a previous measure (e.g. on 0-100 scale as calculated/derived through the system performance measurement algorithm).

In some embodiments, the treatment variable is an analyte level and the acceptable treatment variable value is a range of the analyte levels.

Some embodiments further comprise defining a recommended intervention and automatically determining the selected performance measure as the clinical performance measurement of the selected intervention by comparing the affected treatment variable value to the acceptable treatment variable values and comparing the recommended intervention to the selected intervention. For example, this performance measure reflects how well the intervention affected the treatment variable and how the selected intervention compared to the recommended intervention.

Some embodiments further comprise determining a plurality of affected treatment variable values over a treatment time period, each of the affected treatment variable values associated with one or more time in the treatment time period, determining whether one or more of the plurality of affected treatment variable values is one of a good affected treatment variable (e.g. within target range) value or a bad affected treatment variable value (e.g. outside of target range) and identifying the one or more time wherein the affected treatment variable value is one of a good affected treatment variable value or a bad affected treatment variable value.

Some embodiments further comprise determining a plurality of selection performance measures over a performance time period, each of the selection performance measures associated with one or more time in the performance time period, determining whether one or more of the plurality of selection performance measures is one of a good selection performance measure or a bad selection performance measure and identifying the one or more time wherein the selection performance measure is one of a good selection performance measure or a bad selection performance measure.

Some embodiments also further comprise any of the other analytic methods described herein. For example, some embodiments further comprise identifying a treatment indicator by performing a pattern recognition analysis on the plurality of affected treatment variable values whereby the treatment indicator associates the selected intervention with one of a good affected treatment variable value or a bad affected treatment variable value. And some embodiments, comprise identifying a performance indicator by performing a pattern recognition analysis on the plurality of selected performance measures whereby the performance indicator associates the selected intervention with one of a good selection performance measures or a bad selection measure.

In some embodiments, where the performance measure is determined by an algorithm, a good measure (e.g., selection performance measure, affected treatment variable value) may be the algorithm/routine which is instantiated and used to increase the system derived performance measurement based on favorable healthcare and patient outcomes (e.g. treatment variable maintained within target range). Conversely, a bad measure (e.g., selection performance measure, affected treatment variable value) may be the the algorithm/routine which is instantiated and used to decrease system-derived performance measurement based on unfavorable healthcare and patient outcomes (e.g. treatment variables exceed target range).

Some embodiments configured to provide performance assessments may also further comprise any of the other clinical decision support methods described herein. For example, some embodiments further comprise automatically determining a recommended intervention as the selected intervention before performing the selected intervention.

Some embodiments configured to provide performance assessments may also further comprise any of the other simulation and training methods described herein. For example, in some embodiments the subject is a hypothetical subject, the acceptable treatment variable values are model treatment variable values in a clinical simulation and the clinical performance measurement is a simulated clinical performance measurement of a clinical training simulator. As an example, the methods may be used with a training simulator where the variable values of the subject are hypothetical values stored in a database and the acceptable treatment variable values are predefined values based on normal treatment values for subjects.

Some embodiments configured to provide measurement and assessment methods may also further comprise any of the other analytic methods described herein.

Some embodiments configured to provide measurement and assessment methods may also further comprise any of the user interfaces described herein.

Figure 4:
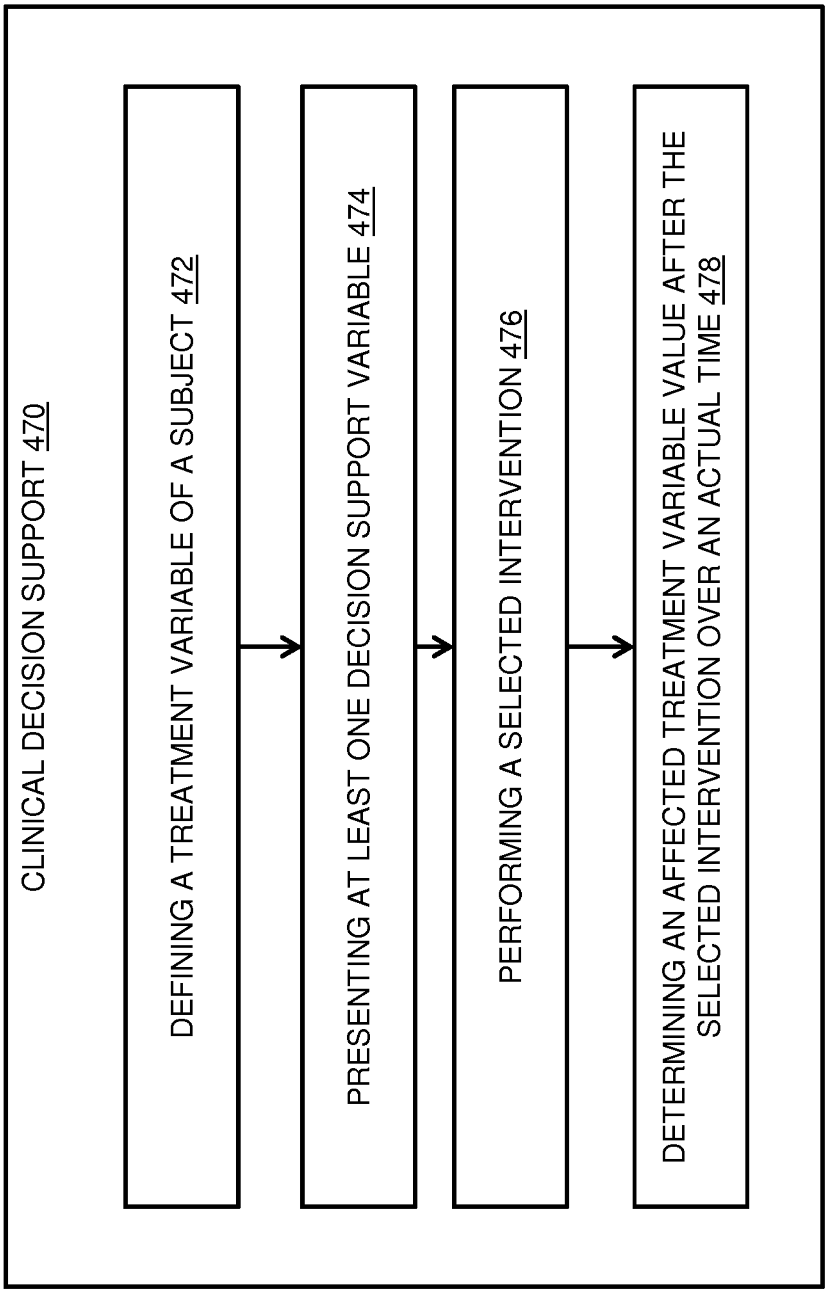
FIG. 4 illustrates a process diagram of one example embodiment of methods for clinical decision support.

An Example Embodiment of the Clinical Support System and Methods, Clinical Decision Support Some embodiments of clinical support methods are configured to provide clinical decision support to system users. As shown in FIG. 4, one example embodiment of clinical decision support at 470 comprises defining a treatment variable of a subject at 472, presenting at least one decision support variable at 474, performing a selected intervention at 476 and determining an affected treatment variable value after the selected intervention over an actual time at 478.

Some embodiments further comprise receiving a set of historical treatment variables of the subject, identifying a trend from the historical treatment variables of the subject and the decision support variable comprises the trend. In some embodiments, identifying a trend/pattern from the historical treatment variables of the subject further comprises utilizing one or a combination of supervised and unsupervised machine learning algorithms and models.

Some embodiments further comprise receiving a set of historical treatment variables of the subject, identifying an event from the historical treatment variables of the subject and the decision support variable comprises the event. In some embodiments, identifying an event from the historical treatment variables of the subject further comprises utilizing one or a combination of supervised and unsupervised machine learning algorithms and models.

Some embodiments further comprise receiving a set of historical treatment variables of the subject, identifying one or more events from the historical treatment variables of the subject, receiving a set of real-time treatment variables of the subject and comparing the one or more events to the set of real-time treatment variables to estimate future expected trends/patterns in treatment variables. Some embodiments further comprise determining a similarity rating between the set of historical treatment variables of the subject and the real-time treatment variables of the subject, defining a similarity rating threshold, identifying one or more of the events that exceed the similarity rating threshold as exceptional events and statistically analyzing the exceptional events to provide an estimation of a future trend. Some embodiments further comprise updating the historical treatment variables with the results of the statistical analysis to produce case-based estimations with higher levels of confidence and accuracy.

In some embodiments, the decision support is a recommended intervention.

Some embodiments further comprise, before performing a selected intervention, presenting a visual representation of at least one additional treatment variable as a clinical decision support.

Some embodiments further comprise defining a recommended intervention and automatically determining a selection performance measure of the selected intervention by comparing the recommended intervention to the selected intervention.

As an illustrative example of an embodiment configured to provide clinical decision support, one example embodiment of clinical support systems and methods presents a visualization of input data such as electronic medical records (EMR) data as one means of providing clinical decision support. An example user interface for this embodiment is shown in FIG. 2A. In this embodiment the overall functionality of the clinical support system displays useful clinical decision information to patients and healthcare providers to better equip them with information to support optimization of clinical decisions and interventions and self-directed (patient-driven) therapies. FIG. 2A demonstrates an embodiment of this user interface for use in the hospital and critical care setting which utilizes pattern recognition algorithms to determine patterns and trends in EMR data. In this user interface, key organ systems are presented to medical personnel (cardiac, renal, endocrine, and pulmonary) of which each have different treatment variables which need to be controlled within target ranges to ensure optimal patient outcomes. In the embodiment presented in FIG. 2A, the medical staff is presented with a view of blood glucose control (a key treatment variable value of the endocrine system). Trend recognition algorithms identify patterns in glucose (chosen treatment variable) based on current patient state (medications, laboratory results, and other key EMR data). The medical staff has the ability to specify to search for patterns in glucose values across a future time horizon within the current patient's historical EMR data, or across historical EMR data within the current patient and similar patients (i.e. patients with similar reasons for admission, length of stay in hospital, age, body mass index, etc.). Medical staff is also presented with divergent patterns (regions where glucose values do not follow identified trend). The user can click these divergent trends to identify differences in EMR data between detected patterns and divergent trends. Additionally, when treatment variables of interest have values that fall outside (or are predicted to fall outside) of target ranges for a particular organ system, the user is alerted to this as the organ system will be outlined in red and flash and alert medical personnel that interventions need to be made.

Some embodiments configured to provide clinical decision support may also further comprise any of the other analytic methods described herein. Some embodiments incorporate presenting at least one decision support variable comprises presenting at least one of a plurality of interventions on the treatment variable, selecting one of the plurality of interventions as a test intervention on the treatment variable, inputting the test intervention into a predictive model, determining an affected test treatment variable value over a selected time by modeling the test intervention on the test treatment variable over the selected time and presenting a visual representation of the affected test treatment variable value over the selected time. Some embodiments further comprise presenting other treatment variable values to further provide clinical decision support.

Some embodiments configured to provide clinical decision support may also further comprise any of the other measurement and assessment methods described herein. Some embodiments incorporate defining a range of an acceptable treatment variable values for the treatment variable and automatically determining a selection performance measure of the selected intervention by comparing the affected treatment variable value to the acceptable treatment variable values.

Some embodiments configured to provide clinical decision support may also further comprise any of the simulation and training methods described herein.

Some embodiments configured to provide clinical decision support may also further comprise any of the user interfaces described herein.

Figure 5:
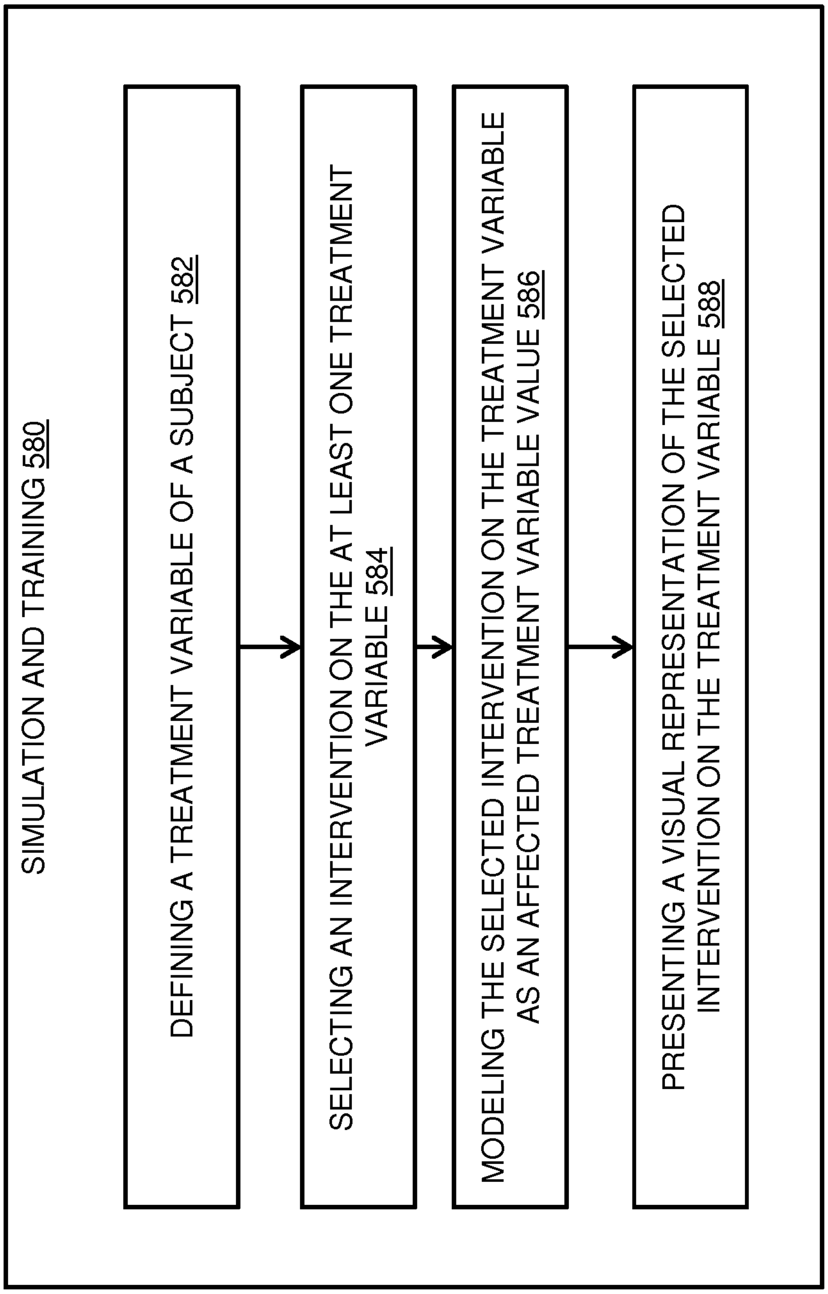
FIG. 5 illustrates a process diagram of one example embodiment of methods for clinical decision support.

An Example Embodiment of the Clinical Support System and Methods, Simulation and Training Some embodiments of clinical support methods are configured to provide simulations and training methods to system users. As shown in FIG. 5, one example embodiment of simulation and training methods 580 comprises defining a treatment variable of a simulated subject at 582, selecting an intervention on the at least one treatment variable at 584, modeling the selected intervention on the treatment variable as an affected treatment variable value at 586 and presenting a visual representation of the selected intervention on the treatment variable at 588.

Some embodiments may also further comprise any of the other analytic methods described herein. Some embodiments incorporate modeling the selected intervention on the treatment variable as an affected treatment variable value comprises modeling the selected intervention on the treatment variable with a machine learning algorithm such as a neural network model.

Some embodiments may also further comprise any of the other analytic and decision support methods described herein. For example, some embodiments further comprise, before selecting the intervention on the treatment variable selecting a test intervention on the treatment variable, inputting the test intervention into a predictive model, determining the affected treatment variable value over a selected time by modeling the test intervention on the affected treatment variable over the selected time and presenting a visual representation of the affected treatment variable value over the selected time. Some embodiments further comprise, before determining the affected treatment variable value over the selected time, automatically determining a recommended intervention as the selected intervention. In some embodiments, automatically determining a recommended intervention as the selected intervention comprises automatically determining a recommend intervention as the selected intervention utilizing a Partially Observable Markov Decision Process (POMDP) algorithm to model the affected treatment variable value (via time-series probabilistic modeling).

Some embodiments may also further comprise any of the other measurement and assessment methods described herein. For example, some embodiments further comprise defining a range of the treatment variable as a range of acceptable treatment variable values and automatically determining a selection performance measure of the intervention by comparing the affected treatment variable value to the acceptable treatment variable values. As another example, some embodiments are configured to evaluate the performance of staff/patients in terms of decision-making and problem solving (i.e. being able to identify when to use or deviate from suggestions generated by clinical decision support system, and using other functionality of decision support system to lead to optimal decision). As another example, some embodiments may provide retrospective and real-time analytics (assessment, measurement, and prediction) of performance and identification of time domains where performance is good or poor (couple with pattern recognition and other algorithms/analytics in system).

Some embodiments configured to provide simulations and training methods may also further comprise any of the clinical decision support methods described herein.

Some embodiments configured to provide simulations and training methods may also further comprise any of the analytic methods described herein.

Some embodiments configured to provide clinical decision support may also further comprise any of the user interfaces described herein.

Figure 6:
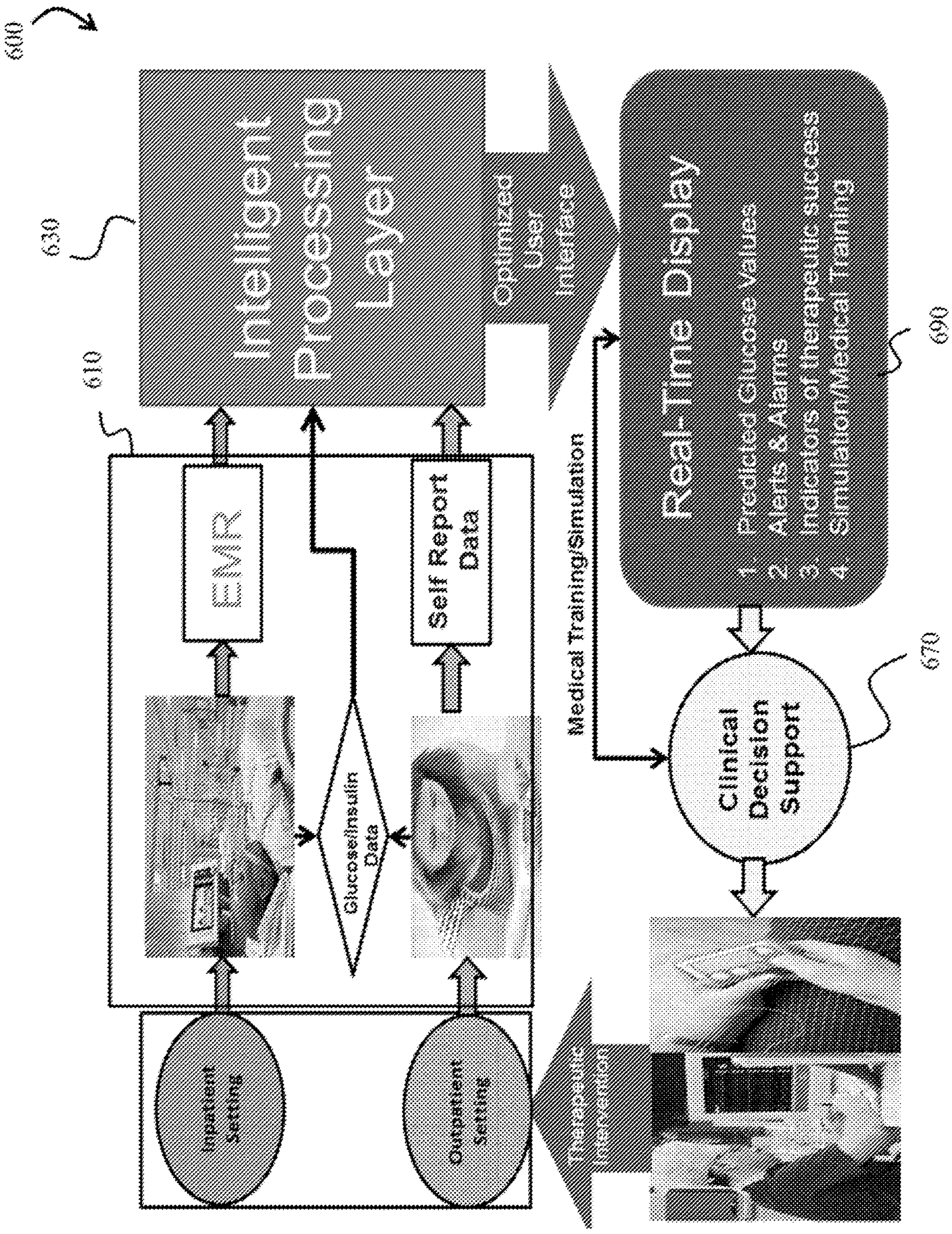
FIG. 6 illustrates one example system architecture of one embodiment of STACDS for supporting inpatient and outpatient glycemic control.

An Example Embodiment of the Clinical Support Methods, Glycemic Control in Inpatient and Outpatient FIG. 6, outlines the functional components of one embodiment of clinical support systems and methods directed to facilitate optimization of glycemic control for a subject in inpatient (e.g. hospital, ICU), and outpatient (patients with diabetes) settings. In this embodiment 600, data sources for input data 610, representing treatment variables, differ between inpatient and outpatient settings in that EMR data is present as the main data source in inpatient settings whereas self-reported (e.g. diet, exercise, stress levels, etc.) values are necessary for outpatient applications. Thus, in inpatient settings the clinical support systems 670 will communicate with EMR databases and in outpatient settings will be configured to communicate with self-report tools (e.g. mobile phones, tablets, etc.) to acquire key information and data to support functionality of the clinical support systems 670. In both settings insulin and glucose monitoring data are common inputs therefore clinical support systems will share these inputs regardless of application. The intelligent processing layer 630 will implement analytic methods such as predictive models and/or pattern recognition algorithms to identify trends in future glucose values. The results of the intelligent processing layer 630 may be presented to the clinical support systems user interface 690 and clinical decision support layer to provide simulation, training, and real-time decision support capabilities.

Figure 7:
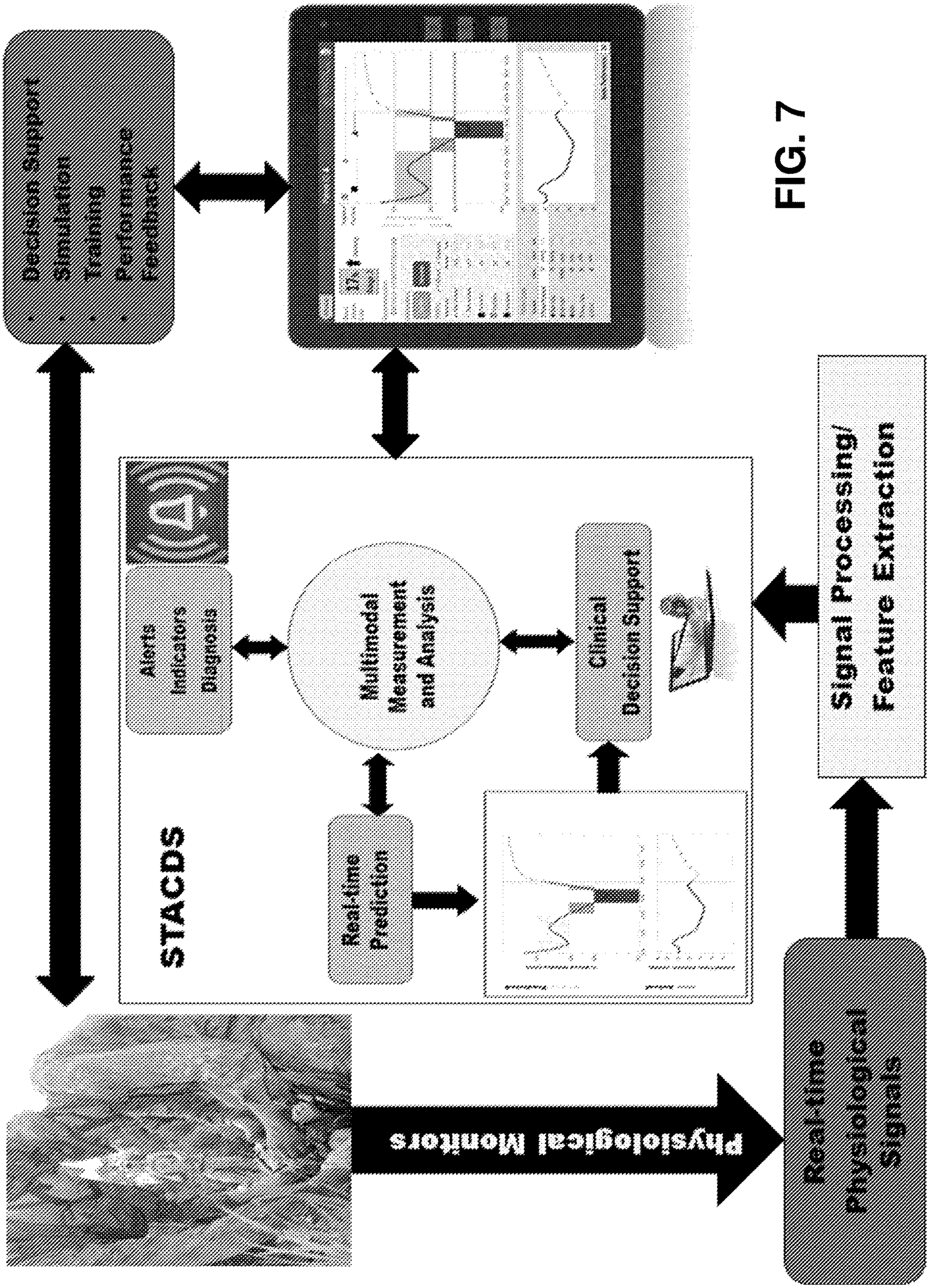
FIG. 7 illustrates one example system architecture of one embodiment of STACDS with applications in military combat casualty care or civilian trauma in patients susceptible to hemorrhagic shock.

An Example Embodiment of the Clinical Support System and Methods, STACDS for Supporting Triage, Fluid Resuscitation, and Outcome in Trauma Patients FIG. 7 demonstrates an alternate embodiment of the STACDS system to facilitate optimization of patient care and outcome in military and civilian trauma patients which are susceptible to uncontrolled bleeding and subsequent hemorrhagic/hypovolemic shock. Here STACDS reads in real-time physiological data acquired from medical monitors, EMR data, etc and implements signal processing to derive key features of these physiological data (e.g. heart rate, pulse pressure, respiration rate etc.). These features are submitted to the major components of the STACDS architecture (Multi-modal measurement and assessment layer, Real-time Prediction Layer, Clinical Decision Support Layer, and Interactive UI). Here, the components interact to provide the comprehensive Simulation, Training, And Clinical Decision Support Capabilities of STACDS.

Figure 8:
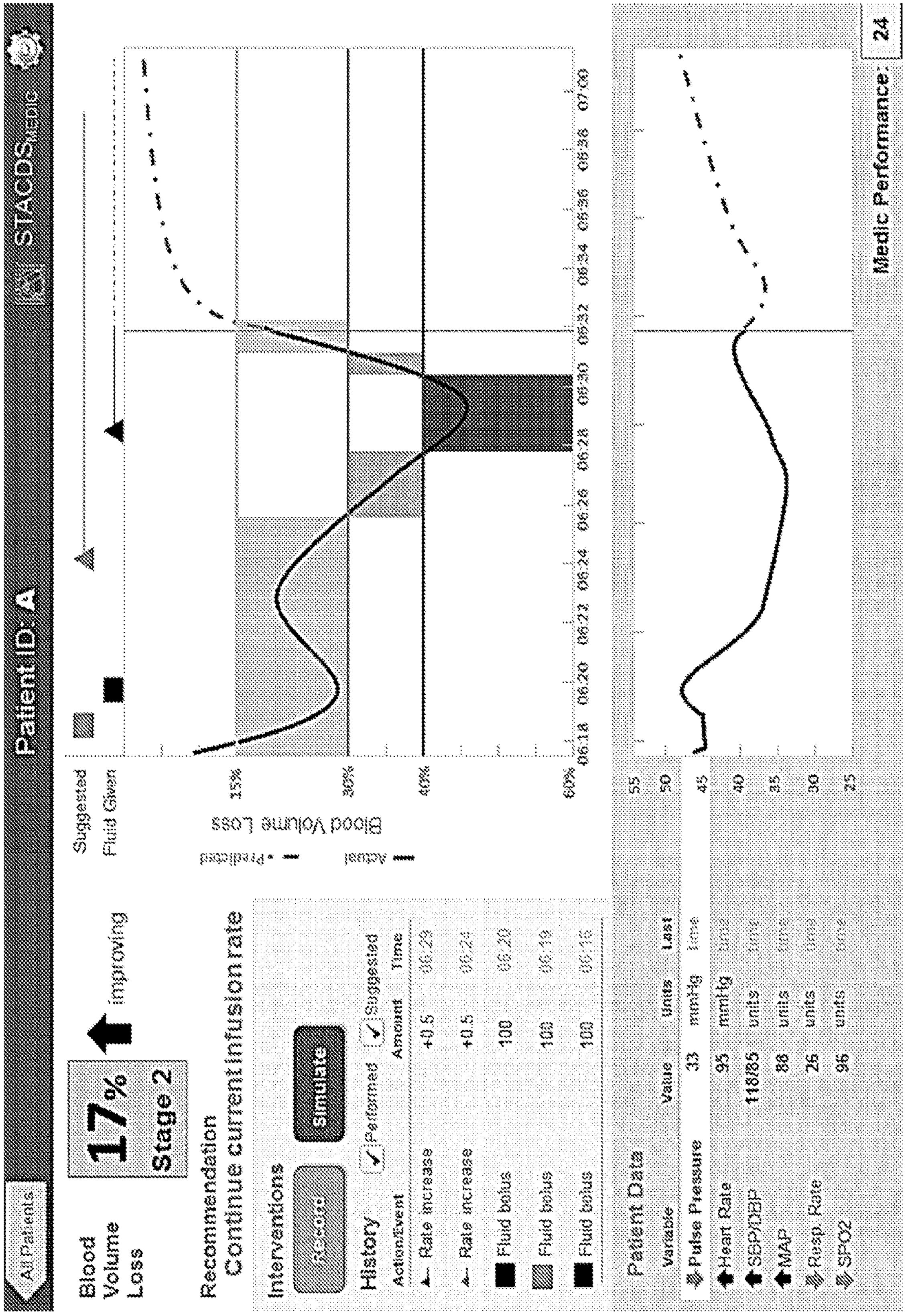
FIG. 8 illustrates one example user interface for one embodiment of STACDS for detection and prediction of hemorrhagic shock in military and civilian trauma applications.

FIG. 7 includes a UI design for the embodiment of STACDS illustrated by FIG. 8. In this embodiment, the individual patient screen contains four sections of information. The upper left section (dark grey background) shows the current percent blood volume loss (% BVL), stage of shock, whether the % BVL is improving or worsening, and an intervention recommendation. The largest panel (white background) shows a graph of % BVL over time and predicted % BVL. When % BVL enters into the range for stages 2, 3, and 4 of shock, the background behind them is color coded. This method of background shading allows medical personnel to get an immediate sense of the general trend of % BVL for that patient, even if viewed from a distance, whereas the trend line alone shows more detail but requires closer scrutiny. Above the graph is a timeline of interventions proposed by the algorithms and actual interventions performed. Squares represent fluid boluses, lines represent continuous infusions, and triangles represent changes in infusion rate. The third section (light grey background) shows the history of interventions and includes buttons to record interventions performed and to simulate interventions. Pushing either of these buttons will produce a pop-up where the medic can enter more details about a specific intervention. The lower panel contains a table of patient data and a line graph that aligns with the % BVL graph. The data table contains key patient physiological features associated with % BVL, and the user can select one variable to graph over time. As with % BVL, predictions of the selected feature are provided in the graph. An indicator in the bottom right of the screen presents a measure of the medic's performance (real-time feedback), which is calculated based on accuracy of decision making, responsivity to alerts, patient monitoring, and maintenance of desirable hemodynamic status.

In this embodiment, the UI design (see FIG. 8) for the individual patient screen contains four sections of information. The upper left section shows the current percent blood volume loss (% BVL), stage of shock, whether the % BVL is improving or worsening, and an intervention recommendation. The largest panel shows a graph of % BVL over time and predicted % BVL. When % BVL enters into the range for stages 2, 3, and 4 of shock, the background behind the line is color coded. This method of background shading allows medical personnel to get an immediate sense of the general trend of % BVL for that patient, even if viewed from a distance, whereas the trend line alone shows more detail but requires closer scrutiny. Above the graph is a timeline of interventions proposed by the algorithms and actual interventions performed. Squares represent fluid boluses, lines represent continuous infusions, and triangles represent changes in infusion rate. The third section shows the history of interventions and includes buttons to record interventions performed and to simulate interventions. Pushing either of these buttons will produce a pop-up where the medic can enter more details about a specific intervention. The lower panel (medium grey background) contains a table of patient data and a line graph that aligns with the % BVL graph. The data table contains key patient physiological features associated with % BVL, and the user can select one variable to graph over time. As with % BVL, predictions of the selected feature are provided in the graph. An indicator in the bottom right of the screen presents a measure of the medic's performance (real-time feedback), which is calculated based on accuracy of decision making, responsiveness to alerts, patient monitoring, and maintenance of desirable hemodynamic status.

Example Embodiments of the Clinical Support System

One embodiment of a clinical support system comprises the STACDS system. As shown in FIG. 9, the system architecture of the STACDS consists of five components performing five portions of the clinical support methods. The five components comprise: 1) performance measurement and assessment layer, 2) analytics layer, 3) clinical decision support layer, 4) user interface (UI), and 5) simulation and training layer. These components function and communicate with each other to ensure STACDS' functionality and utility in supporting simulation, training, and clinical decision support. FIG. 9 illustrates the interconnectivity of these components and the flow of data between them.

As will be readily apparent to those skilled in the art, the clinical support systems and methods can be embodied in hardware, software, or a combination of hardware and software. For example, a computer system or server system, or other apparatus combining hardware and software adapted for carrying out the methods described herein, may be suitable. One embodiment of a combination of hardware and software could be a general purpose computer system with a computer program that, when loaded and executed, carries out the respective methods described herein. In some embodiments, a specific use computer, containing specialized hardware for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

Figure 10:
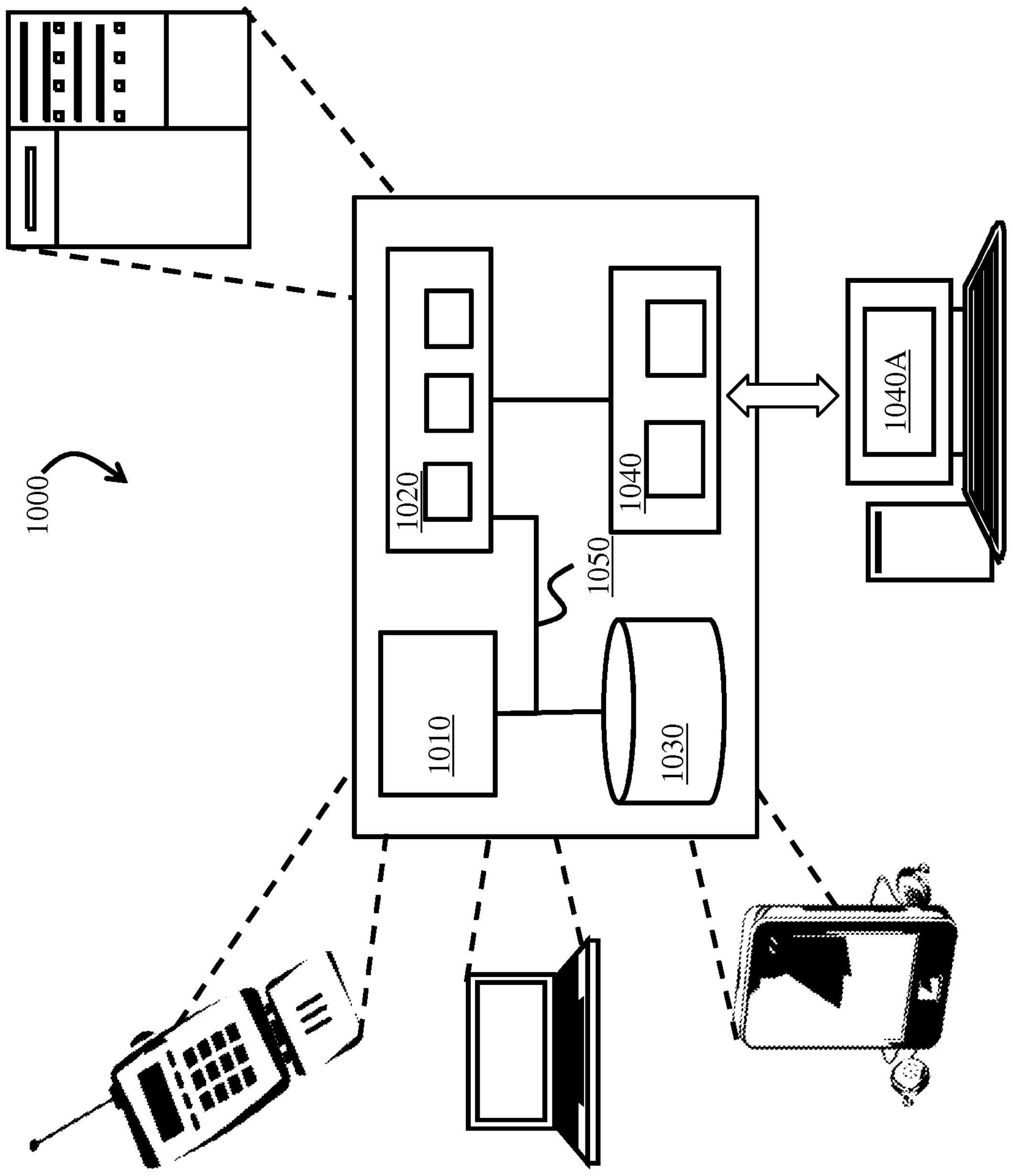
FIG. 10 illustrates one example embodiment of a computer system suitable for use with the STACDS system.

FIG. 10 is a schematic diagram of one embodiment of a computer system 1000 by which the methods of clinical support may be carried out. The computer system 1000 can be used for the operations described in association with any of the computer implemented methods described herein. The computer system 1000 includes at least one processor 1010, a memory 1020 and an input/output device 1040. Each of the components 1010, 1020, and 1040 are operably coupled or interconnected using a system bus 1050. The computer system 1000 may further comprise a storage device 1030 operably coupled or interconnected with the system bus 1050.

The processor 1010 is capable of receiving the instructions and/or data and processing the instructions of a computer program for execution within the computer system 1000. In one embodiment, the processor 1010 is a single-threaded processor. In another embodiment, the processor 1010 is a multi-threaded processor. The processor 1010 is capable of processing instructions of a computer stored in the memory 1020 or on the storage device 1030 to communicate information to the input/output device 1040. Suitable processors for the execution of the computer program instruction include, by way of example, both general and special purpose microprocessors, and a sole processor or one of multiple processors of any kind of computer.

The memory 1020 stores information within the computer system 1000. Memory 1020 may comprise a magnetic disk such as an internal hard disk or removable disk; a magneto-optical disk; an optical disk; or a semiconductor memory device such as PROM, EPROM, EEPROM or a flash memory device. In some embodiments, the memory 1020 comprises a transitory or non-transitory computer readable medium. In one embodiment, the memory 1020 is a volatile memory unit. In another embodiment, the memory 1020 is a non-volatile memory unit.

The processor 1010 and the memory 1020 can be supplemented by, or incorporated in, ASICs (application-specific integrated circuits).

The storage device 1030 may be capable of providing mass storage for the computer system 1000. In various different embodiments, the storage device 1030 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 1030 comprises a transitory or non-transitory computer readable medium.

In some embodiments, the memory 1020 and/or the storage device 1030 may be located on a remote system such as a server system, coupled to the processor 1010 via a network interface, such as an Ethernet interface.

The input/output device 1040 provides input/output operations for the computer system 1000 and may be in communication with a user interface 1040A as shown. In one embodiment, the input/output device 1040 includes a keyboard and/or pointing device. In other embodiments, the input/output device 1040 includes a display unit for displaying graphical user interfaces or the input/output device 1040 comprises a touchscreen. In some embodiments, the user interface 1040A comprises devices such as, but not limited to a keyboard, pointing device, display device or a touchscreen that provides a user with the ability to communicate with the input/output device 1040.

The computer system 1000 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, wireless phone networks and the computers and networks forming the Internet.

In some embodiments, the clinical support system comprises a processor and a non-transitory computer readable medium having a computer readable program code embodied therein, said computer readable program code configured to be executed implement the clinical support methods disclosed herein. In some embodiments, a computer program product is provided for clinical support comprising a computer readable medium having a computer readable program code embodied therein, said computer readable program code configured to be executed to implement the clinical support methods disclosed herein.

Figure 11:
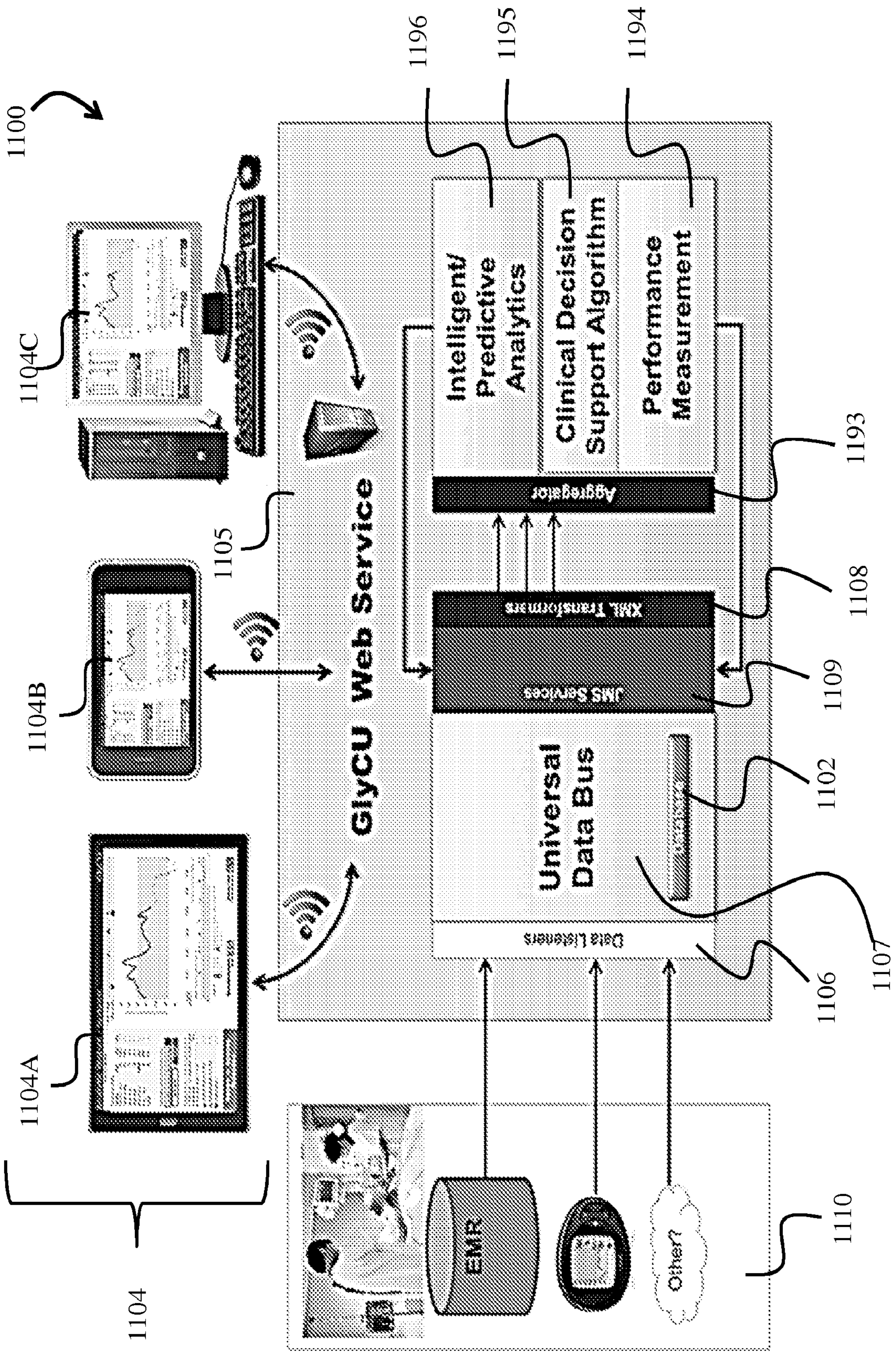
FIG. 11 illustrates an overview of a functional architecture of one embodiment of the clinical support systems embodied in a software program product.

FIG. 11 illustrates an overview of a functional architecture of one embodiment of the clinical support systems embodied in a software program product made available to users as a web service. As shown, this embodiment generally includes a user interface, such as a web based client 1104 in communication with a server 1105 comprising the software program product configured to execute the system methods. The treatment variables 1110 are able to be communicated to the server 1105 and received through an input/output device, here identified as data listeners 1106. A universal serial bus 1107 operably connects the data listeners 1106, a database 1102, a processer and a memory configured to execute services such as Java Messaging Service (JMS) 1109 and Extensible Markup Language (XML) transformers 1108. The JMS Services 1109 communicate the treatment variables 1110 so that they can be used by the software program product. As shown, the software program product is configured to receive treatment variables via an aggregator 1193 and execute: the measurement and assessment methods described herein, here identified as Performance Measurement functions 1194; the clinical decision support methods described herein, here identified as Clinical Decision Support Algorithm 1195; and the analytic methods described herein, here identified as Intelligent/Predictive Analytics 1196. The system is also configured to communicate the results of the software program product methods back to the universal serial bus 1107 so that the results may be stored in the database 1102, used as treatment variables 1110 or to be shared with the service clients 1104. In this embodiment, the service clients 1104 are configured to display the results of the system methods. It is understood that the client 1104 may be any user interface capable of communicating with the server and may comprise, for example only, a table interface 1104A, a digital phone interface 1104B or a computer display 1104C. It is understood that embodiments of the clinical support systems are able to receive treatment variables 1110 from the clients 1104.

The clinical support system of FIG. 11 may serve as a comprehensive clinical decision support software and web service which readily integrates on the front end of a healthcare institution's electronic medical records (EMR) system. This embodiment is designed to support healthcare staff in optimizing glycemic control in the hospital/critical care setting. This embodiment provides unique and comprehensive functionality through implementation of: 1.) intelligent and advanced analytics which provides both short term (75 minutes ahead) and long term (>24 hours) prediction and identification of trends/patterns in glucose and other related EMR data; 2.) advanced clinical decision support algorithms which account for uncertainty in data and guide healthcare staff in making optimal treatment decisions; 3.) optimized and algorithm-driven visualization of EMR designed to minimize cognitive overload of healthcare staff and present useful trends in data to support optimal decision making; 4.) healthcare personnel-centered real-time and retrospective simulation and training capabilities; and 5.) real-time and retrospective measurement/assessment of healthcare staff performance in meeting therapeutic goals. This embodiment is a web-based software solution and application supporting comprehensive clinical decision support. As a web-based application, this embodiment will enable healthcare personnel to access the complete functionality of the clinical support system remotely from any computer or mobile device through the hospital's secure local network, or via secure login through any available internet access point. This embodiment may be designed to be completely hardware and software agnostic and can be readily integrated with a healthcare institution's EMR system, and any current and future patient monitoring technology.

JMS services in the diagram correspond to the Java Messaging Service which is a way to send and transmit data to the decision support system components based on real-time data which is queried from the data sources listed above in real-time. Overall, this allows us to collect and time-sync data from all of these data sources in a common messaging format based on known locations of data on a network or system. This is integral to us connecting the system in real-time to query data sources such as the hospital EMR database where data is received at different rates and frequencies.

Although the above embodiments may be described a separate embodiments, it is understood that the above example embodiments may be implements separately and may be implemented in combinations of those embodiments.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

I claim:

1. A computer implemented method for clinical performance measurement of a clinician treating a patient subject, said method comprising:

defining a range of an acceptable treatment variable values for a treatment variable of the patient subject;

the treatment variable is an analyte level of the patient subject's blood and the acceptable treatment variable values is a range of the analyte level;

the clinician selecting a selected intervention for the patient subject;

the clinician performing the selected intervention on the patient subject;

the selected intervention comprising a medicine change for the patient subject;

determining an affected treatment variable value for the treatment variable of the patient subject from a sensor after performing the selected intervention;

a processor based clinical support system modeling the selected intervention on the treatment variable over a predicted time with a predictive model;

the predictive model trained with a plurality of affected treatment variable values of the patient subject;

determining, with the predictive model, a plurality of predicted affected treatment variable values over the predicted time;

the processor based clinical support system automatically determining a selection performance measure as the clinical performance measurement of the clinician for the selected intervention by comparing the affected treatment variable value and the plurality of predicted affected treatment variable values to the acceptable treatment variable values;

performing a plurality of selected interventions on the patient subject over a performance time period;

determining a plurality of the selection performance measures over the performance time period;

each of the plurality of the selection performance measures associated with one or more time in the performance time period;

determining whether one or more of the plurality of the selection performance measures is one of a good selection performance measure or a bad selection performance measure wherein the good selection performance measure is correlated with one of the predicted affected treatment variable values being within the acceptable treatment variable values and the bad selection performance measure is correlated with one of the predicted affected treatment variable values being outside of the acceptable treatment variable values;

identifying a performance indicator by performing a first pattern recognition analysis on the plurality of selected interventions and the plurality of the selection performance measures over the performance time period whereby the performance indicator identifies an association of one or more of the plurality of selected interventions with one or more of the good selection performance measure or the bad selection performance measure;

the first pattern recognition analysis comprises a stochastic search algorithm configured to compare and find patterns between the plurality of the selection performance measures and the treatment variable value comprises a predicted future analyte level existent in a historical dataset of treatment variable values;

the clinician performing the plurality of selected interventions on the patient subject over a treatment time period;

determining the plurality of affected treatment variable values over the treatment time period;

identifying the one or more time wherein the affected treatment variable value is one of a good affected treatment variable value or a bad affected treatment variable value;

identifying a treatment indicator by performing a second pattern recognition analysis on the plurality of selected interventions on the patient subject and the plurality of affected treatment variable values at the one or more time over the treatment time period whereby the treatment indicator identifies an association of one or more of the plurality of selected interventions with one or more of the good affected treatment variable value or the bad affected treatment variable value; and the second pattern recognition analysis comprises a second stochastic search algorithm configured to find patterns of the plurality of selected interventions on the patient subject to compare to a plurality of historical selected interventions from a historical dataset of selected interventions and the treatment variable values comprises a predicted future analyte level value existent in the historical dataset of treatment variable values.

2. The method of claim 1 further comprising:

defining a recommended intervention; and automatically determining the selection performance measure as the clinical performance measurement of the clinician for the selected intervention by comparing the affected treatment variable values to the acceptable treatment variable values IDC- and comparing the recommended intervention to the selected intervention.

3. The method of claim 1 further comprising:

receiving a plurality of treatment variable values for the treatment variable over a treatment time period;

each of the treatment variable values associated with one or more time in the treatment time period; and storing the treatment variable values associated with one or more time in the treatment time period whereby the plurality of treatment variable values may be played back as associated with the one or more time in the the treatment time period.

4. The computer implemented method of claim 1 further comprising presenting a visual representation of at least one additional treatment variable value selected from the group consisting of:

a treatment data;

an emotional data;
a lifestyle data;
an observed data;
a self-reported data;
an electronic medical record (EMR) data;
a personal health records (PHR) data;
a nutrition data;
a medication data; and
a nursing scale.

5. The computer implemented method of claim 1 wherein:
the patient subject is a hypothetical subject;
the acceptable treatment variable values are model treatment variable values in a clinical simulation; and
the clinical performance measurement of the clinician is a simulated clinical performance measurement of a clinical training simulator.

6. The computer implemented method of claim 1 further comprising automatically determining a recommended intervention as the selected intervention before performing the selected intervention.

7. The computer implemented method of claim 6 wherein automatically determining the recommended intervention as the selected intervention comprises automatically determining the recommend intervention as the selected intervention utilizing a control system model to model the affected treatment variable value.

8. The computer implemented method of claim 6 wherein automatically determining the recommended intervention as the selected intervention comprises automatically determining the recommended intervention as the selected intervention utilizing a Partially Observable Markov Decision Process (POMDP) algorithm to model the affected treatment variable value.

9. The computer implemented method of claim 1 further comprising, before performing the selected intervention on the treatment variable:
presenting a visual representation of the affected treatment variable value over the selected time.

10. The computer implemented method of claim 9 wherein the predictive model comprises a machine learning algorithm.

11. The computer implemented method of claim 9 wherein the predictive model comprises a neural network.

12. The computer implemented method of claim 9 further comprising, before performing the selected intervention on the treatment variable, presenting a visual representation of at least one additional treatment variable selected from the group consisting of:
a treatment data;
an emotional data;
a lifestyle data;
an observed data;
a self-reported data;
an electronic medical record (EMR) data;
a personal health records (PHR) data;
a nutrition data;
a medication data; and
a nursing scale.

13. The computer implemented method of claim 9 wherein:
the patient subject is a hypothetical subject; the acceptable treatment variable values are model treatment variable values of a clinical simulation; and
the clinical performance measurement of the clinician is a simulated clinical performance measurement of a clinical training simulator.

14. The computer implemented method of claim 1 further comprising, before selecting the intervention on the treatment variable:
selecting a test intervention on the treatment variable;
inputting the test intervention into the predictive model;
determining the affected treatment variable value over the predicted time by modeling the test intervention on the affected treatment variable value over the predicted time;
and presenting a visual representation of the affected treatment variable value over the predicted time.

15. The method of claim 1 wherein the treatment indicator comprises:
a numeric representation of the association of one or more of the selected interventions with one or more of the good affected treatment variable value or the bad affected treatment variable value; and
the affected treatment variable value comprises a glycated hemoglobin A1C level.

* * * * *